United States Patent
Saulnier et al.

(10) Patent No.: US 6,677,450 B2
(45) Date of Patent: Jan. 13, 2004

(54) TOPOISOMERASE INHIBITORS

(75) Inventors: Mark G. Saulnier, Higganum, CT (US); Edward H. Ruediger, Greenfield Park (CA); Neelakantan Balasubramanian, Madison, CT (US); Mikael Mahler, Outremont (CA); Francis Beaulieu, Laprairie (CA); Carol Bachand, Candiac (CA); David B. Frennesson, Naugatuck, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/965,976

(22) Filed: Sep. 27, 2001

(65) Prior Publication Data

US 2002/0107237 A1 Aug. 8, 2002

Related U.S. Application Data

(60) Provisional application No. 60/238,726, filed on Oct. 6, 2000.

(51) Int. Cl.$^7$ .......................... C07H 9/06; C07H 19/23; C07D 498/22
(52) U.S. Cl. ..................................... 540/545
(58) Field of Search ........................ 540/545

(56) References Cited

U.S. PATENT DOCUMENTS

| | | | |
|---|---|---|---|
| 4,487,925 A | 12/1984 | Nettleton, Jr. et al. | 536/24 |
| 4,552,842 A | 11/1985 | Nettleton, Jr. et al. | 435/75 |
| 4,567,143 A | 1/1986 | Matson | 435/119 |
| 4,785,085 A | 11/1988 | Kaneko et al. | 536/23 |
| 5,043,335 A | 8/1991 | Kleinschroth et al. | 514/211 |
| 5,407,940 A | 4/1995 | Bisagni et al. | 514/285 |
| 5,468,849 A | 11/1995 | Lam et al. | 536/18.5 |
| 5,468,872 A | 11/1995 | Glicksman et al. | 548/416 |
| 5,475,110 A | 12/1995 | Hudkins et al. | 546/256 |
| 5,478,813 A | 12/1995 | Okanishi et al. | 514/43 |
| 5,498,611 A | 3/1996 | Bisagni et al. | 514/232.8 |
| 5,589,365 A | 12/1996 | Kojiri et al. | 435/85 |
| 5,618,809 A * | 4/1997 | Barrabee et al. | 514/211 |
| 5,668,271 A | 9/1997 | Kojiri et al. | 536/27.1 |
| 5,674,867 A * | 10/1997 | Tamaoki et al. | 514/219 |
| 6,037,468 A * | 3/2000 | Wood et al. | 540/545 |

FOREIGN PATENT DOCUMENTS

| | | |
|---|---|---|
| EP | 0 450 327 A1 | 10/1991 |
| EP | 0602597 A2 | 12/1993 |
| EP | 0545195 B1 | 11/1995 |
| EP | 1101770 A | 5/2001 |
| WO | WO 89/07105 * | 10/1989 |
| WO | WO 95/30682 | 11/1995 |
| WO | WO 96/04293 | 2/1996 |
| WO | WO 96/11933 | 4/1996 |
| WO | WO 98/07433 | 2/1998 |
| WO | WO 99/02532 * | 1/1999 |

OTHER PUBLICATIONS

Anizon et al. (Bioorganic & Medicinal Chemistry (1998), 6(9), 1597–1604).*
Long, et al., *American Association for Cancer Research Proceedings* (1997), 38: 75 Abstract.
Madden, et al., *Cancer Research* (1992), 52: 525–532.
O'Connor, et al., *Cancer Communications* (1990), 2: 395–400.
Pollack, et al., *Molecular Pharmacology* (1999), 56: 185–195.
Prudhomme, M., *Current Medicinal Chemistry* (2000), 7: 1189–1212.
Abstract of Hungary 203758 (Sep. 1991).
B. B. Shankar, S. W. McCombie, *Tetrahedron Lett.* (1994), 35: 3005.
B. M. Stolz, J. L. Wood, *Tetrahedron Lett.* (1995), 36: 8543.
J. Anizon, et al., *Bioorg. & Med. Chem.* (1998), 6: 1597.
S. W. McCombie, et al., *Bioorg. & Med. Chem. Lett.* (1993), 8: 1537.
C. Bailly, et al., *Biochem.*, (1997), 36: 3917.
D. Von Hoff, et al., *Cancer Chemother., Pharmacol.*(1994), 34 (suppl): S41.
T. Yoshinari, et al., *Cancer Research*, (1993), 53: 490.
T. Yoshinaru, et al., *Cancer Research*, (1995), 55: 1310.
D.A. Scudiero, et al, *Cancer Research*, (1988), 48: 4827.
R.L. Halcomb et al., *J. Am. Chem. Soc.* (1989), 111: 6661.
E.R. Pereira, et al, *J. Med. Chem.*, (1996), 39: 4471.
Greene and Wuts, Protective Groups in Organic Synthesis, 2$^{nd}$ Ed., John Wiley and Sons and McOmie, New York, 1991.
J. L. Wood, et al., *J. Am. Chem. Soc.* (1995), 117: 10413.
J. T. Link, et al., *J. Am. Chem. Soc.* (1996), 118: 2825.
R. Kobayoshi, et al., *J. Am. Chem. Soc.* (1999), 121: 6501.
A. Mazur and G. Hiler, *J. Org. Chem.* (1997), 62: 4471.
K. Nowak, et al., *Roczniki Chem.*, (1969), 43: 1953.
M. Gallant, et al., *J. Org. Chem.*, (1993), 58: 343.
M.S. Motawia, et al., *J. Carbohydrate Chemistry*, (1995), 14(9): 1279.
K.C. Nicolau, et al., *J. Amer Chem. Soc.*, (1989) 111: 6661.
S. F. Vice, et al., *Bioorg. Med. Chem. Lett.* (1994), 4: 1333.
T. Hayashi, et al., *Bioorganic And Medicinal Chemistry*, (1997), 5(3): 497.
Weinreb, et al., *Heterocycles* (1984), 21: 309.
Y.–H. Hsiang, et al, *J. Biol. Chem.*, (1985), 260(27): 14873.

* cited by examiner

*Primary Examiner*—Bruck Kifle
(74) *Attorney, Agent, or Firm*—Shah Makujina; Kenneth W. Peist

(57) ABSTRACT

The present invention relates to novel N12, N13-bridged sugar derivatives of indolylopyrrolocarbazoles and pharmaceutical formulations thereof which exhibit topoisomerase-I activity and are useful in inhibiting the proliferation of tumor cells.

9 Claims, No Drawings

TOPOISOMERASE INHIBITORS

RELATED APPLICATIONS

This application claims priority benefit under Title 35 § 119(e) of U.S. provisional Application No. 60/238,726, filed Oct. 6, 2000. The contents of which are herein incorporated by reference.

FIELD OF THE INVENTION

The present invention relates to sugar derivatives of indolopyrrolocarbazoles which exhibit topoisomerase I activity and are useful in inhibiting the proliferation of tumor cells.

BACKGROUND

Topoisomerases are vital nuclear enzymes which function to resolve topological dilemmas in DNA, such as overwinding, underwinding and catenation, which normally arise during replication, transcription and perhaps other DNA processes. These enzymes allow DNA to relax by forming enzyme-bridged strand breaks that act as transient gates or pivotal points for the passage of other DNA strands. Topoisomerase-targeting drugs appear to interfere with this breakage-reunion reaction of DNA topoisomerases. In the presence of topoisomerase active agents, an aborted reaction intermediate, termed a 'cleavable complex', accumulates and results in replication/transcription arrest, which ultimately leads to cell death.

The development of topoisomerase I active agents therefore offers a new approach to the multi-regimental arsenal of therapies currently used in the clinic for the treatment of cancer. An article in Cancer Chemother. Pharmacol [1994, 34 (suppl): S 41–S 45] discusses topoisomerase I active compounds that are in clinical studies and these have been found to be effective clinical anti-tumor agents. Structurally these clinical candidates are related to the alkaloid camptothecin.

Indolo[2,3-a]carbazole derivatives related to the Rebeccamycin class are disclosed (EP Appl. 0 545 195 B1 and 0,602,597 A2; Cancer Research 1993, 53, 490–494; ibid 1995, 55, 1310–1315) and claimed to exhibit anti-tumor activity; however the major mechanism of action of these derivatives may not be like camptothecin, which acts as a topoisomerase I poison.

Indolo[2,3-a]carbazole alkaloids such as rebeccamycin (U.S. Pat. Nos. 4,487,925 and 4,552,842) and its water-soluble, clinically-active analog, 6-(2-diethylaminoethyl) rebeccamycin (U.S. Pat. No. 4,785,085), are useful antitumor agents which target DNA. Furthermore, fluoroindolocarbazoles such as described in WO 98/07433 are antineoplastic agents with topoisomerase I inhibitory activity. Indolocarbazoles are also disclosed (WO 9530682) and claimed to exhibit anti-tumor activity. Hudkins, et al. have disclosed a series of fused pyrrolocarbazoles (WO 96/11933 and U.S. Pat. No. 5,475,110) and showed in vitro biological data such as inhibition of neuronal choline acetyltransferase (ChAT) and protein kinase C (PKC) inhibition for some compounds. U.S. Pat. No. 5,468,849 discloses certain fluororebeccamycin analogs as useful antitumor agents, along with a process for their production by fluorotryptophan analog feeding of a rebeccamycin-producing strain of Saccharothrix aerocolonigenes, preferably Saccharothrix aerocolonigenes C38,383-RK2 (ATCC 39243). Glicksman, et al. disclose indolocarbazole alkaloids (U.S. Pat. No. 5,468,872) which are different in structure from those of the present invention. Kojiri, et al. disclose indolopyrrolocarbazoles having a dissacharide substituent (WO 96/04293). Weinreb, et al. (Heterocycles 1984, 21, 309) and Kleinschroth, et al. (U.S. Pat. No. 5,043,335) have disclosed indolopyrrolocarbazole derivatives with a bridging furan moiety and McCombie, et al. (Bioorg. Med. Chem. Lett. 1993, 3, 1537) have reported a more functionalized bridged furan. Wood, et al. have reported the total synthesis of (+)-K252a (J. Am. Chem. Soc. 1995, 117, 10413), a related, naturally-occurring indolocarbazole alkaloid which has demonstrated PKC inhibitory activity. During the course of their total synthesis of (+)-K252a, Fukuyama, et al. (J. Am. Chem. Soc. 1999, 121, 6501) have also described the isolation of a cycloglycoside as an undesired product.

Danishefsky, et al., during the course of their first total synthesis of staurosporine (J. Am. Chem. Soc. 1996, 118, 2825), describe the synthesis of an intermediate N12, N13-bridged indolopyrrolocarbazole. Indolocarbazole derivatives with the nitrogens linked by a three-atom bridge have been reported to be potent PKC inhibitors (S. F. Vice, et al. Bioorg. Med. Chem. Lett. 1994, 4, 1333). The synthesis of simple indolocarbazole derivatives with C1', C-5'-bridging or C1', C3'-bridging glycosides have also been reported in the literature (B. M. Stolz, J. L. Wood Tetrahedron Lett. 1995, 36, 8543 and B. B. Shankar, S. W. McCombie Tetrahedron Lett. 1994, 35, 3005, respectively). Prudhomme, et al. disclose a series of antitumor indolocarbazoles derived from rebeccamycin which exhibit a carbohydrate attached to the two indole nitrogens, and reported their cytotoxicity and their topoisomerase I and PKC inhibitory activities to be in the millimolar to micromolar range (Bioorg. Med. Chem. 1998, 6, 1597). Despite these examples, there remains a need for novel and potent cytotoxic compounds useful for inhibiting topoisomerase I activity.

SUMMARY OF THE INVENTION

Thus according to a first embodiment of the first aspect of the present invention are provided compounds of Formula (I) and pharmaceutically acceptable salts and solvates thereof, useful for inhibiting topoisomerase I and the proliferation of tumor cells

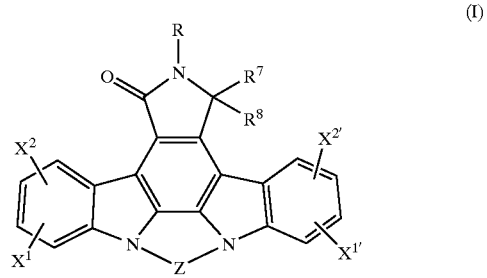

wherein

Z is selected from the group consisting of Formula (A), Formula (B), Formula (C), Formula (D), Formula (E), Formula (F) and Formula (G)

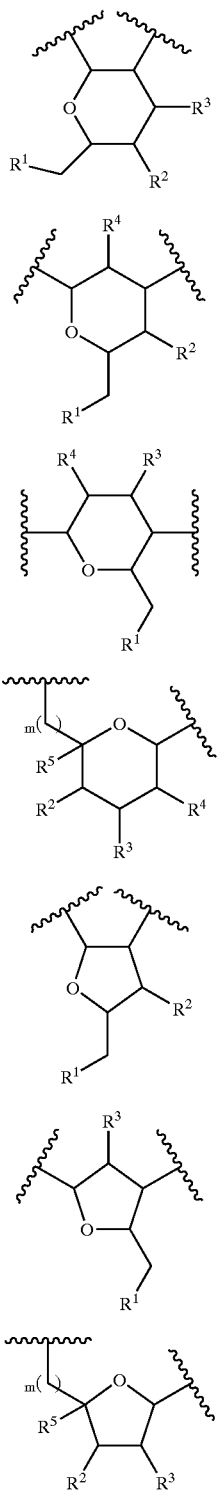

(A)
(B)
(C)
(D)
(E)
(F)
(G)

R is hydrogen, OH, $OC_{1-7}$alkyl, $NH_2$, $N(C_{1-3}$alkyl$)_2$, or $C_{1-7}$alkyl, wherein said $C_{1-7}$alkyl or $C_{1-3}$alkyl is optionally substituted with one or more substituents selected from the group consisting of halogen, CN, $SR^9$, $OR^9$ and $NR^9R^{10}$;

$R^1$, $R^2$, $R^3$, $R^4$ and $R^5$ are each independently selected from the group consisting of hydrogen, $C_{1-7}$alkyl, $C_{3-7}$cycloalkyl, halogen, azido, $NR^9R^{10}$, NHC(O)
$NR^9R^{10}$, $NHC(O)OR^9$, $C(O)OR^9$, $SR^9$ and $OR^9$, wherein said $C_{1-7}$alkyl is optionally substituted with one or more substituents selected from the group consisting of halogen, CN, $SR^9$, $OR^9$ and $NR^9R^{10}$;

provided that no more than two of the variables selected from the group consisting of $R^1$, $R^2$, $R^3$, $R^4$ and $R^5$ may be $C_{3-7}$cycloalkyl, azido, NHC(O)$NR^9R^{10}$ or $NHC(O)OR^9$;

$R^7$ and $R^8$ are independently OH or H or $R^7$ and $R^8$ together form $=O$;

$R^9$ and $R^{10}$ are independently selected from the group consisting of hydrogen, $C_{1-7}$alkyl and $C_{3-7}$cycloalkyl, wherein said $C_{1-7}$alkyl is optionally substituted with one or more substituents selected from the group consisting of halogen, CN, OH, O—$C_{1-7}$alkyl, $NH_2$ and $N(C_{1-3}$alkyl$)_2$; or $R^9$ and $R^{10}$ together with the nitrogen atom to which they are attached form a non-aromatic 5–8 membered heterocycle containing one or two of the same or different heteroatoms selected from the group consisting of O, N and S;

m is 0 or 1; and $X^1$, $X^{1'}$, $X^2$ and $X^{2'}$ are independently selected from the group consisting of hydrogen, halogen, cyano, $OR^9$, —$CF_3$, alkylcarbonyl, $C_{1-7}$alkyl, nitro, alkoxyaminoalkyl, $NR^9R^{10}$, $SR^9$ and $C(O)OR^9$; wherein said $C_{1-7}$alkyl is optionally substituted with one or more substituents selected from the group consisting of halogen, CN, $OR^9$, $SR^9$ and $NR^9R^{10}$.

According to a first embodiment of the first aspect of the present invention are provided compounds of Formula (I) wherein Z is selected from the group consisting of Formula (A), Formula (C) and Formula (D).

According to another embodiment of the first aspect of the present invention are provided compounds of Formula (I) wherein Z is formula (A).

According to another embodiment of the first aspect of the present invention are provided compounds of Formula (I) wherein Z is formula (B).

According to another embodiment of the first aspect of the present invention are provided compounds of Formula (I) wherein Z is formula (C).

According to another embodiment of the first aspect of the present invention are provided compounds of Formula (I) wherein Z is formula (D).

According to another embodiment of the first aspect of the present invention are provided compounds of Formula (I) wherein m is 1.

According to another embodiment of the first aspect of the present invention are provided compounds of Formula (I) wherein m is 0.

According to another embodiment of the first aspect of the present invention are provided compounds of Formula (I) wherein R is hydrogen.

According to another embodiment of the first aspect of the present invention are provided compounds of Formula (I) wherein $R^7$ and $R^8$ together are $=O$.

According to another embodiment of the first aspect of the present invention are provided compounds of Formula (I) wherein $R^7$ and $R^8$ are each H.

According to another embodiment of the first aspect of the present invention are provided compounds of Formula (I) wherein $X^{2'}$ and $X^2$ are each F and $X^1$ and $X^{1'}$ are each H.

According to another embodiment of the first aspect of the present invention are provided compounds of Formula (I) wherein $X^2$ is F and $X^{2'}$, $X^1$ and $X^{1'}$ are each H.

According to another embodiment of the first aspect of the present invention are provided compounds of Formula (I) wherein $X^{2'}$ is F and $X^2$, $X^1$ and $X^{1'}$ are each H.

According to another embodiment of the first aspect of the present invention are provided compounds of Formula (I) wherein $X^{2'}$, $X^2$, $X^1$ and $X^{1'}$ are each F.

According to another embodiment of the first aspect of the present invention are provided compounds of Formula (I) wherein $X^{2'}$ and $X^2$ are each H and $X^1$ and $X^{1'}$ are each F.

According to another embodiment of the first aspect of the present invention are provided compounds of Formula (I) wherein $R^1$, $R^2$, $R^3$, $R^4$ and $R^5$ are independently selected from the group consisting of H, F, $OR^9$ wherein $R^9$ is hydrogen or methyl.

Other embodiments of the first aspect of the present invention provide compounds of Formula (I) comprising two or more of the above embodiments of the first aspect suitably combined.

Embodiments of a second aspect of the present invention provide a method for inhibiting tumor growth in a mammalian host, particularly a human host, comprising the administration to said host of a tumor-growth inhibiting amount of a compound of the present invention, as defined herein.

Embodiments of a third aspect of the present invention provide a method for inhibiting tumor growth in a mammalian host comprising the administration to said host of a tumor-growth inhibiting amount of a pharmaceutical formulation of a compound of the present invention, as defined in the embodiments of the first aspect of the invention.

Other embodiments and aspects of the invention will be apparent according to the description provided below.

DETAILED DESCRIPTION OF THE INVENTION

The description of the invention herein should be construed in congruity with the laws and principals of chemical bonding. An embodiment or aspect which depends from another embodiment or aspect, will describe only the variables having values and provisos that differ from the embodiment or aspect from which it depends. Thus, for example, an embodiment which reads "the compound of formula (I) according to the $n^{th}$ aspect of the invention, wherein R is $NH_2$" should be read to include all remaining variables with values defined in the $n^{th}$ aspect and should be read to further include all the provisos, unless otherwise indicated, pertaining to each and every variable in the $n^{th}$ aspect. Where a variable is defined as having a value of zero, it is understood that the bond attached to said variable should be removed. For example, if n=0 and R—X—$V_n$ wherein n can be 0 or 1, then it is understood that the structure described is R—X not R—X—. The numbers in the subscript after the symbol "C" define the number of carbon atoms a particular group can contain. For example "$C_{1-7}$alkyl" means a straight or branched saturated carbon chain having from one to seven carbon atoms including without limitation groups such as methyl, ethyl, n-propyl, isopropyl, n-butyl, sec-butyl, isobutyl, t-butyl, n-pentyl, sec-pentyl, isopentyl, n-hexyl and n-heptyl. "Aryl" means an aromatic hydrocarbon having from six to ten carbon atoms; examples include phenyl and naphthyl. "Substituted aryl" or "substituted aralkyl" means an aryl or aralkyl group independently substituted with one to five (but particularly one to three) groups selected from the group consisting of $C_{1-6}$alkanoyloxy, hydroxy, halogen, $C_{1-6}$ alkyl, trifluoromethyl, $C_{1-6}$alkoxy, $C_{2-6}$alkenyl, $C_{1-6}$alkanoyl, nitro, amino, cyano, azido, $C_{1-6}$ alkylamino, and amido. The term "halogen" includes fluoro, chloro, bromo and iodo.

It is to be understood that the present invention includes any and all possible stereoisomers, geometric isomers, diastereoisomers, enantiomers and anomers, unless a particular description specifies otherwise.

The compounds of this invention can exist in the form of pharmaceutically acceptable salts. Such salts include addition salts with inorganic acids such as, for example, hydrochloric acid and sulfuric acid, and with organic acids such as, for example, acetic acid, citric acid, methanesulfonic acid, toluenesulfonic acid, tartaric acid and maleic acid. Further, in case the compounds of this invention contain an acidic group, the acidic group can exist in the form of an alkali metal salt such as, for example, a potassium salt and a sodium salt; an alkaline earth metal salts such as, for example, a magnesium salt and a calcium salt; and salts with organic bases, such as a triethylammonium salt and an arginine salt. The compounds of the present invention may be hydrated or non-hydrated.

The compounds of this invention can be administered in such oral dosage forms as tablets, capsules (each of which includes sustained release or timed release formulations), pills, powders, granules, elixirs, tinctures, suspensions, syrups and emulsions. The compounds of this invention may also be administered intravenously, intraperitoneally, subcutaneously, or intramuscularly, all using using dosage forms well known to those of ordinary skill in the pharmaceutical arts. The compounds can be administered alone but generally will be administered with a pharmaceutical carrier selected upon the basis of the chosen route of administration and standard pharmaceutical practice. Compounds of this invention can also be administered in intranasal form by topical use of suitable intranasal vehicles, or by transdermal routes, using transdermal skin patches. When compounds of this invention are administered transdermally the dosage will be continuous throughout the dosage regimen.

One aspect of the present invention involves administration of the compounds of the present invention, or pharmaceutically acceptable salts or solvates thereof, to a mammal implanted with a tumor or susceptible to cancer formation. In general the compound would be given in a dose range of from about 0.01 mg/kg to about the MTD (maximum tolerated dose). The dosage and dosage regimen and scheduling of a compound of the present invention must in each case be carefully adjusted, utilizing sound professional judgment and considering the age, weight and condition of the recipient, the route of administration and the nature or extent of the cancer disease condition. The term "systemic administration" as used herein refers to oral sublingual, buccal, transnasal, transdermal, rectal, intramascular, intravenous, intraventricular, intrathecal, and subcutaneous routes. In accordance with good clinical practice, it is preferred to administer the instant compounds at a concentration level which will produce effective beneficial effects without causing any harmful or untoward side effects.

DETAILED DESCRIPTION

Procedures for the preparation of Formula (I) compounds are illustrated in Schemes 1–6 and the preparation of the key intermediates/starting materials is illustrated in Scheme 7.

SCHEME 1
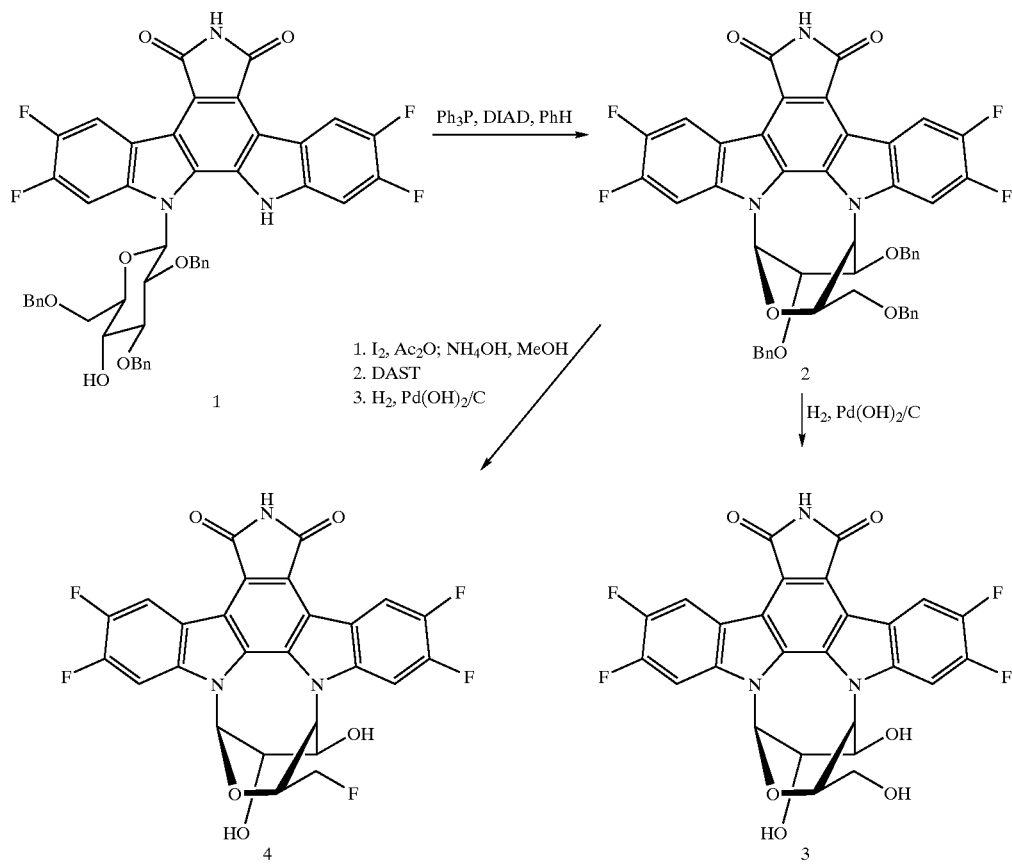
SCHEME 2
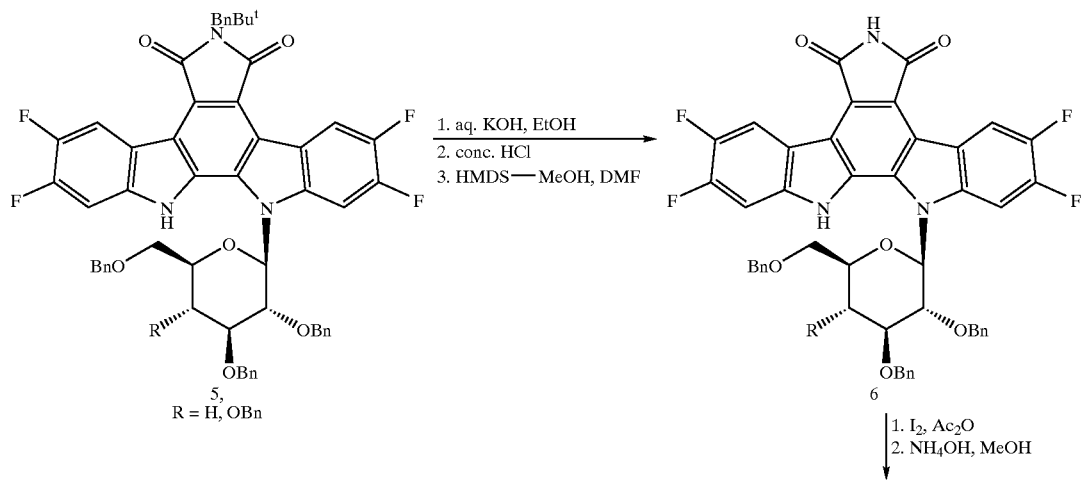

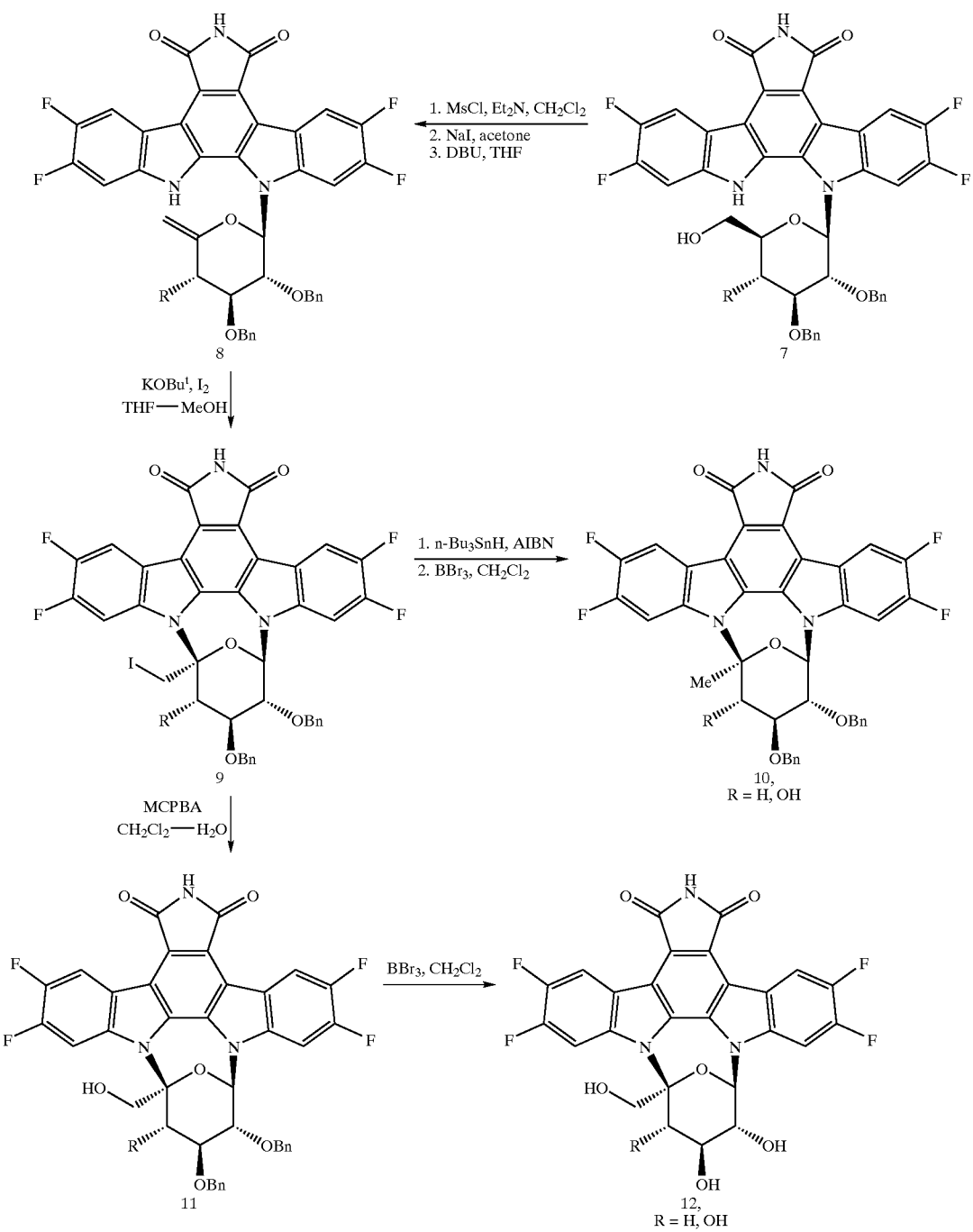

SCHEME 3
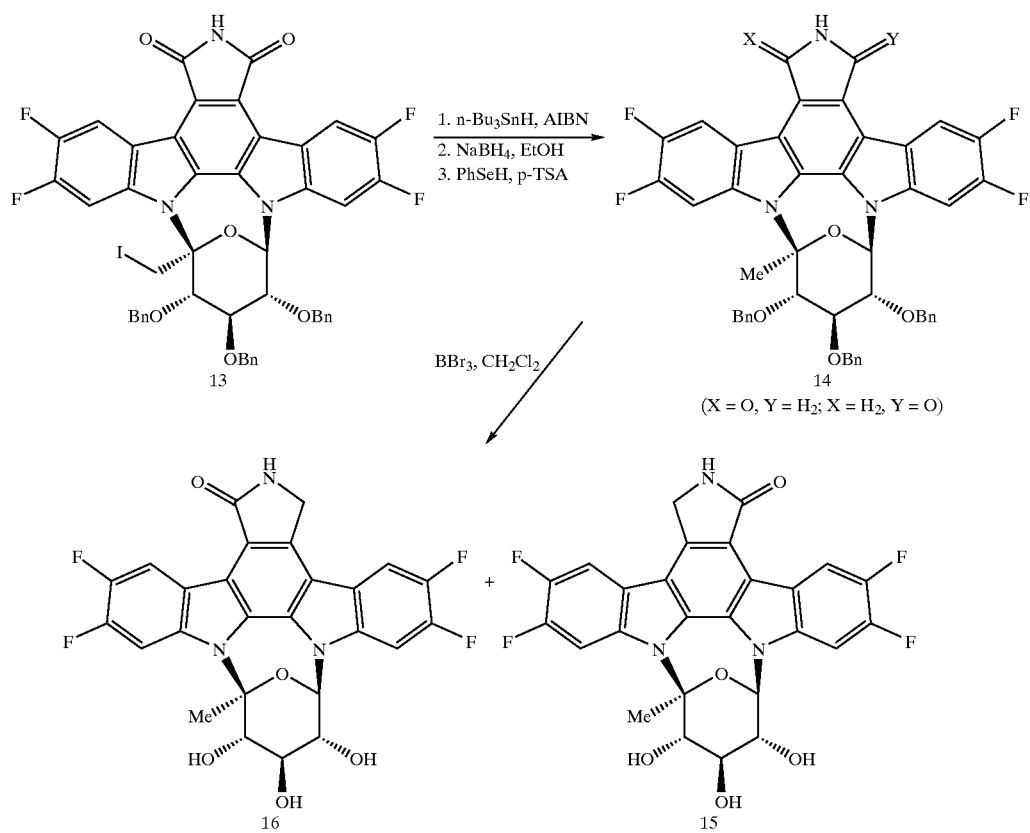
SCHEME 4
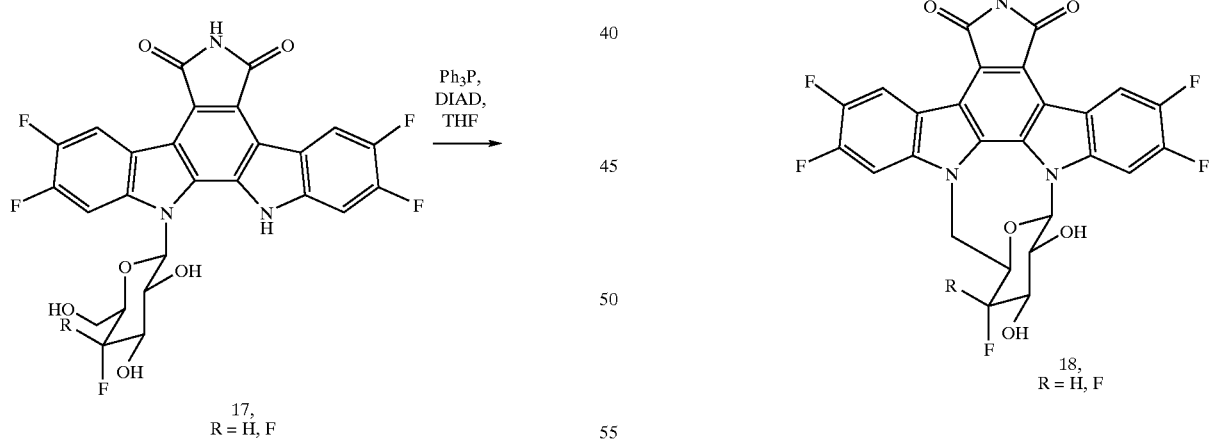

SCHEME 5
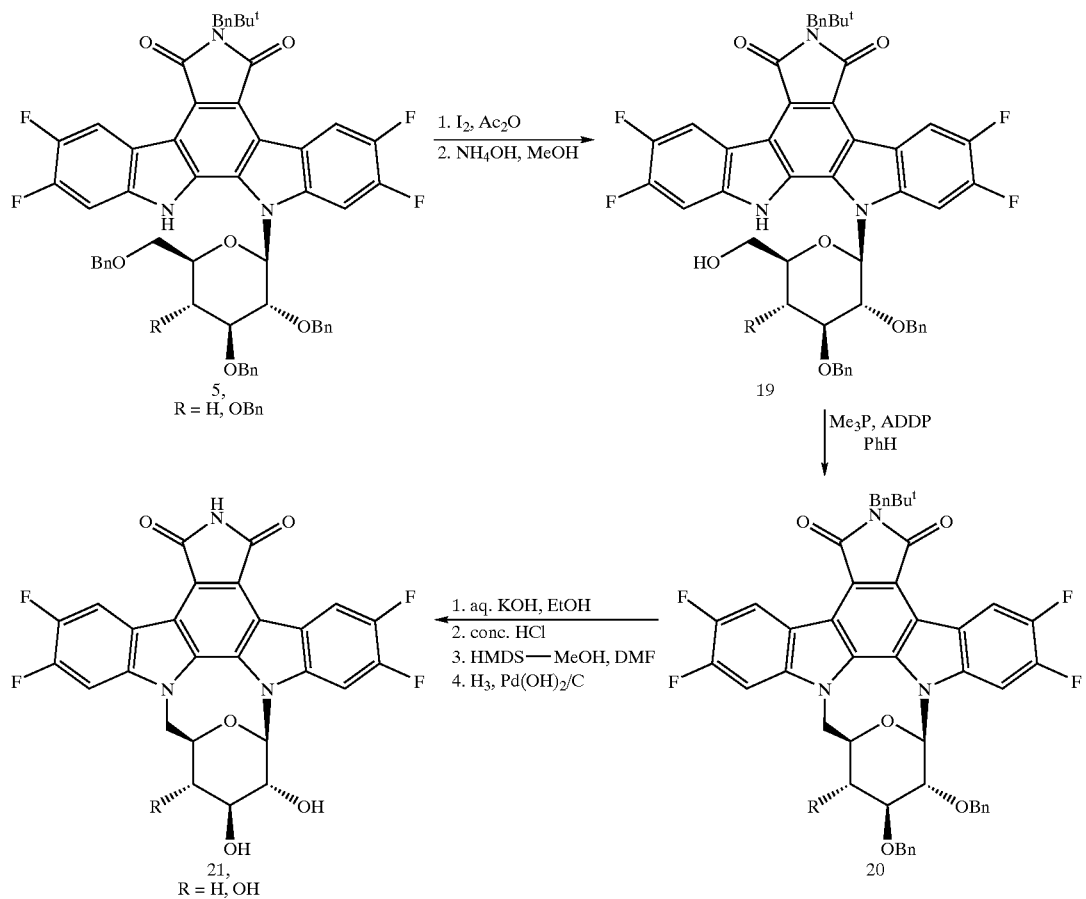
SCHEME 6
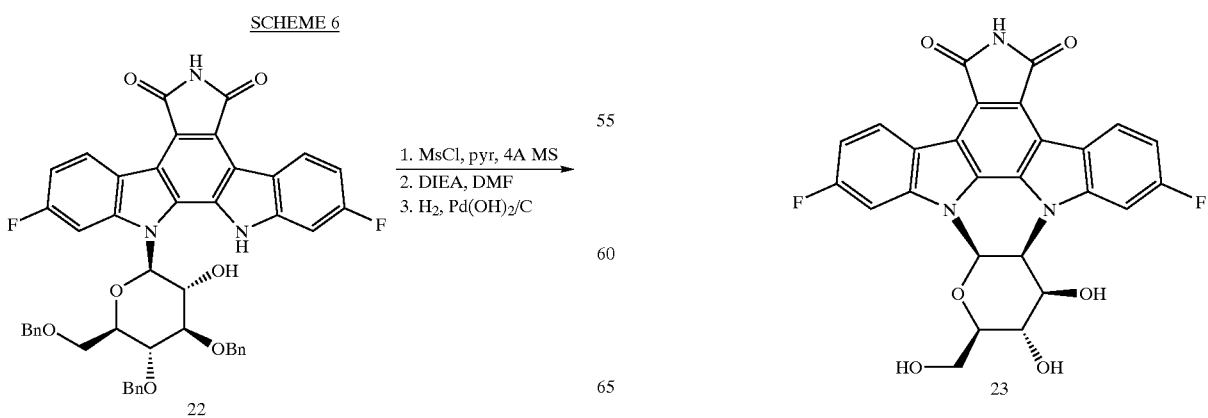

SCHEME 7

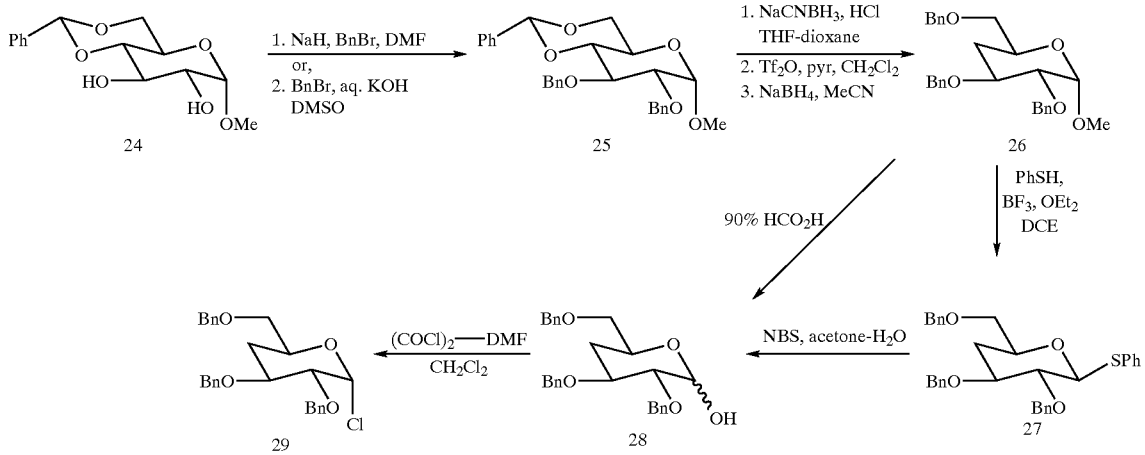

In Scheme 1, a selectively protected glycoside (1) was treated under Mitsunobu conditions (cf. O. Mitsunobu *Synth.*, 1981, 1, 1), for example using triphenylphosphine and diisopropyl azodicarboxylate (DIAD), in a suitable solvent like benzene at room temperature to 100° C., preferably at or around 80° C., to give a 4'-bridged glycoside (2). Removal of the benzyl protecting groups could then be done using a conventional procedure involving hydrogenolysis over Pearlman's catalyst (20% Pd(OH)$_2$ on charcoal) to give a fully deprotected bridged glycoside (3). Alternatively, a partially deprotected glycoside could be prepared by treatment of the corresponding perbenzylated glycoside with iodine in acetic anhydride (cf. K. P. R. Kartha, R. A. Field *Tetrahedron* 1997, 53, 11753), followed by hydrolysis of the intermediate acetate. Subsequent treatment of this selectively deprotected glycoside with the well-known fluorinating agent DAST [(diethylamino)sulfur trifluoride], followed by debenzylation as before, then gives a monofluorinated bridged glycoside (4).

An alternative bridging procedure is shown in Scheme 2. Deprotection of the imide moiety of perbenzylated glycosides such as 5 was done by base-induced hydrolysis, followed by acidification to give an intermediate anhydride. The latter was conveniently converted to an imide using a suitable amine, such as that provided by reaction with a mixture of hexamethyldisilazane and methanol in dimethylformamide (cf. P. D Davis, R. A. Bit *Tetrahedron Lett.* 1990, 31, 5201). Selectively deprotected glycosides like 7 could then be prepared by treatment of the corresponding perbenzylated glycosides with iodine in acetic anhydride (cf. K. P. R. Kartha, R. A. Field *Tetrahedron* 1997, 53, 11753), followed by hydrolysis of the intermediate acetates. The resulting primary alcohol could then be activated, for example as its mesylate and subsequently the corresponding iodide, and induced to undergo elimination of the element of HI using a suitable amine base, such as 1,8-diazabicyclo [5.4.0]undec-7-ene (DBU), to give a vinyl ether 8. Treatment of this vinyl ether with iodine, in the presence of a suitable base such as potassium tert-butoxide, leads to a bridging reaction to give a 1',5'-bridged glycoside 9. The resulting iodide (9) readily undergoes a radical-induced reduction, using for instance tri-n-butyltin hydride as the hydride source and 2,2'-azobisisobutyronitrile (AIBN) as a radical initiator, to give the corresponding 6'-deoxy bridged glycoside. Final removal of the benzyl protecting groups to give 10 could be effected using a number of standard methods, for example by treatment with boron tribromide. Alternatively, the iodide 9 could also be readily oxidized using a peracid, such as m-chloroperbenzoic acid, to give a 6'-hydroxy-substituted bridged glycoside (11). Final deprotection as before then gives derivative 12.

The aromatic core is also readily reduced as shown in Scheme 3. Following radical reduction of the iodide 13, the imide moiety is reduced by treatment with a reducing hydride, such as sodium borohydride, with further reduction using benzeneselenol to give a mixture of the corresponding lactams. Final deprotection as before then gives a mixture of the regioisomeric lactams 15 and 16.

In some instances, unprotected glycosides may conveniently be used to prepare bridged glycosides. For instance, as shown in Scheme 4, an unprotected glycoside (17) cyclizes under the previously mentioned Mitsunobu reaction conditions to give a 1',6'-bridged glycoside (18). This strategy is advantageous in that it obviates the need for a final deprotection step.

Another useful approach to the synthesis 1',6'-bridged glycosides is shown in Scheme 5. In this case, the previously mentioned glycoside (5) is mono-debenzylated as described before to give the 6'-deprotected glycoside 19. The latter undergoes a bridging reaction to give 20 under Mitsunobu conditions, for example by the use of a complex of trimethylphosphine and 1,1'-(azodicarbonyl)dipiperidine (ADDP) in a suitable solvent, such as benzene, at room temperature to around 100° C., preferably at or about 80° C. Removal of all of the benzyl protecting groups is then done as before to give the 1',6'-bridged glycoside 21.

Mono-debenzylated glycosides may also be used to prepare selected bridged glycosides as shown in Scheme 6. Thus, the unprotected hydroxyl group of the tri-O-benzylglycoside 22 could be activated, for example as its mesylate, which may then undergo elimination of the element of methanesulfonic acid using a suitable amine base, such as diisopropylethylamine, to give a 1',2'-bridged glycoside which is readily debenzylated as before to give 23.

A key intermediate sugar was prepared as shown in Scheme 7. Conversion of a commercially available methyl-α-D-glucopyranoside (24) to a 4-deoxyglycoside (26) was done as reported by Barrette and Goodman (*J. Org. Chem.* 1984, 49, 176). Deprotection of the anomeric position could be done in two steps, first by treatment with benzenethiol and a Lewis acid, such as boron trifluoride etherate (cf. L. A. Paquette, J. A. Oplinger *J. Org. Chem.* 1988, 53, 2953), followed by hydrolysis of the resulting phenylthio sugar derivative (27) using N-bromosuccinimide in a suitable solvent, such as acetone or acetonitrile, in the presence of water (cf. B. Fraser-Reid, et al. *J. Am. Chem. Soc.* 1988, 110, 2662). Alternatively, deprotection of the anomeric position could be effected in one step by treatment with a suitable acid, such as 90% formic acid, to give the glucopyranoside (28) directly. Conversion of a glycopyranoside, such as 28, to a glycopyranosyl chloride (29) could be done according to a procedure reported by Iversen and Bundle (*Carb. Res.* 1982, 103, 29).

The compounds which constitute this invention and their methods of preparation will appear more fully from a consideration of the following examples which are given for the purpose of illustration only and are not to be construed as in any way limiting the scope of the invention.

SYNTHESIS OF INTERMEDIATES

Several intermediate compounds as well as other conventional starting materials, used in the preparation of final products of Formula I, were generally known in the literature or were commercially available. Representative syntheses of some of these compounds are nevertheless provided hereinbelow.

All anhydrous reactions were performed under an atmosphere of nitrogen or argon using either commercially available dry solvents or freshly distilled solvents. Melting points were determined in an open capillary tube with a Thomas-Hoover melting point apparatus and are uncorrected. Column chromatography was performed using EM Science silica gel 60 (230–400 mesh) with the designated solvent system as eluant. Thin-layer chromatography was done on E. Merck silica gel 60 $F_{254}$ plates (0.5 mm). Hplc purity determinations were done using either a Shimadzu LC-10AS with a SPD-10AV UV-Vis detector and one of the following columns; YMC Combiscreen ODS-A (4.6×50 mm), or HP Zorbax SB-C18 (4.6×750 mm); or, an HP 1090 DR5 with a diode array detector and a Waters Nova-Pak C18 column (3.9×150 mm). Infrared spectra were recorded on a Nicolet Protégé 460 FTIR as thin films or KBr pellets. $^1$HNMR spectra were recorded on either a Bruker AMX-400 or a Bruker ARX-500 NMR spectrometer and chemical shifts are expressed in parts per million (ppm or δ) with the solvent in use as internal standard. Coupling constants are given in hertz (Hz) and multiplets are designated as follows; singlet (s), doublet (d), triplet (t), quartet (q), muliplet (m), and broad (br). Low resolution mass spectra were determined on a Finnigan Matt TSQ-7000 triple stage quadrapole spectrometer (positive/negative ESI) operated in the negative ion mode.

EXAMPLE 1

6-(4-tert-Butylbenzyl)-2,3,9,10-tetrafluoro-12,13-[1,6-(2,3, 4-tri-O-benzyl-β-D-glucopyranosyl)]-6,7,12,13-tetrahydro (5H)indolo[2,3-a]pyrrolo[3,4-c]carbazole-5,7-dione

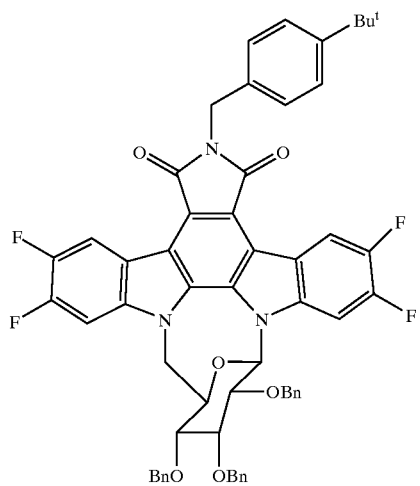

To a solution of 6-(4-tert-butylbenzyl)-2,3,9,10-tetrafluoro-12-(2,3,4-tri-O-benzyl-β-D-glucopyranosyl)-6,7,12,13-tetrahydro(5H)indolo[2,3-a]pyrrolo[3,4-c]carbazole-5,7-dione (0.377 g, 0.39 mmol) in 10 mL of dry benzene was added a solution of trimethylphosphine (1 M in THF, 0.78 mL, 0.78 mmol), followed by solid 1,1'-(azodicarbonyl) dipiperidine (ADDP) (0.227 mg, 0.90 mmol). After stirring at room temperature under Ar for 5 min, the resulting blood-red mixture was heated to reflux for 30 min. The cooled yellow-orange mixture was applied directly onto a silica gel flash column. Elution with dichloromethane afforded the title compound (0.276 g, 74%) as a bright yellow glass:

$^1$H NMR (CDCl$_3$, 400 MHz) δ9.07 (dd, J=10.5, 8.4 Hz, 1H), 8.99 (dd, J=10.5, 8.3 Hz, 1H), 7.7–7.3 (m, 15H), 6.82 (br s, 3H), 6.47 (br s, 2H), 6.27 (m, 1H), 5.99 (d, J=7.7 Hz, 1H), 5.00 (d, J=12.7 Hz, 1H), 4.99 (d, J=11.0 Hz, 1H), 4.96 (d, J=11.0 Hz, 1H), 4.82 (d, J=12.6 Hz, 1H), 4.81 (d, J=15.0 Hz, 1H), 4.73 (d, J=14.7 Hz, 1H), 4.61 (m, 1H), 4.45 (br s, 1H), 4.18–4.11 (m, 2H), 3.97–3.92 (m, 4H), 1.26 (s, 9H).

EXAMPLE 2

2,3,9,10-Tetrafluoro-12,13-[1,6-(2,3,4-tri-O-benzyl-β-D-glucopyranosyl)]-6,7,12,13-tetrahydro(5H)indolo[2,3-a] pyrrolo[3,4-c]carbazole-5,7-dione

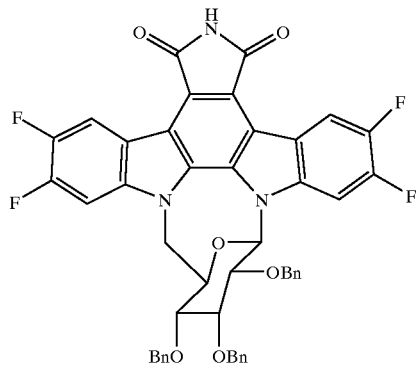

To a solution of 6-(4-tert-butylbenzyl)-2,3,9,10-tetrafluoro-12,13-[1,6-(2,3,4-tri-O-benzyl-β-D-glucopyranosyl)]-6,7, 12,13-tetrahydro(5H)indolo[2,3-a]pyrrolo[3,4-c]-carbazole-5,7-dione (0.276 g, 0.29 mmol) in 20 mL of ethanol-THF (1:1) was added 5 mL of 5 M KOH solution. The resulting mixture was heated to reflux under Ar for 2 h while the THF was gradually allowed to distill off (Dean-Stark trap). The reaction mixture was cooled at 0° C., acidified with conc. HCl and then diluted with ethyl acetate. This mixture was vigorously stirred at r.t. for 1 h and then the organic phase was separated and the aqueous phase was re-extracted with ethyl acetate. The combined organic phase was washed (brine), dried ($Na_2SO_4$) and evaporated to give a solid. The solid was taken up in dichloromethane-acetonitrile and the solution was concentrated to give a precipitate. The solid was filtered, washed with a little acetonitrile and dried in vacuo to give 195 mg (83%) of the anhydride as a bright yellow solid. To a solution of this anhydride in 10 mL of dry DMF was added methanol (0.105 mL, 10 equiv), followed by hexamethyldisilazane (1.09 mL, 20 equiv). After being stirred at r.t. for 7 h, the mixture was partitioned with ethyl acetate-saturated aqueous $NH_4Cl$, the organic phase was separated and the aqueous phase was re-extracted with ethyl acetate. The combined organic phase was washed (brine), dried ($Na_2SO_4$) and evaporated to give a solid. Flash chromatography ($SiO_2$/dichloromethane-ethyl acetate, 1:0 then 4:1) afforded the pure product (0.183 g, 78% overall) as a yellow glass:

$^1$H NMR ($CDCl_3$, 400 MHz) δ8.87 (m, 1H), 8.74 (m, 1H), 7.8–7.3 (m, 12H), 7.12 (br, 1H), 7.00 (br, 2H), 6.65 (br, 1H), 6.30 (br, 1H), 5.98 (d, J=7.4 Hz, 1H), 4.99 (m, 3H), 4.80 (d, J=_12.5 Hz, 1H), 4.54 (br s, 2H), 4.25–3.85 (m, 6H).

MS (ESI$^-$) m/e 810 (M–H)$^-$.

EXAMPLE 3

2,3,9,10-Tetrafluoro-12,13-(1,6-β-D-glucopyranosyl)-6,7,12,13-tetrahydro(5H)indolo[2,3-a]pyrrolo[3,4-c]carbazole-5,7-dione

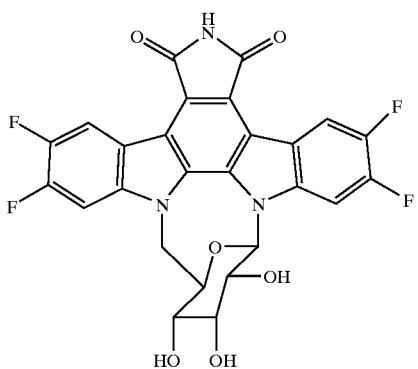

To a solution of 2,3,9,10-tetrafluoro-12,13-[1,6-(2,3,4-tri-O-benzyl-β-D-glucopyranosyl)]-6,7,12,13-tetrahydro(5H) indolo[2,3-a]pyrrolo[3,4-c]carbazole-5,7-dione (0.086 g, 0.106 mmol) in 40 mL of chloroform-methanol (1:1) was added 20% Pd(OH)$_2$/C (0.090 g) and the mixture was hydrogenated (balloon pressure) at room temperature with vigorous stirring for 72 h. The resulting mixture was then filtered (Celite) and the cake was washed successively with methanol, THF and again with methanol. Evaporation of the filtrate gave a brownish-yellow gum which was taken up in a little methanol to give a solid. The solid was filtered, washed with a little methanol and dried in vacuo to give the title compound as a yellow solid. The filtrate was evaporated and the residue again taken up in a minimum volume of methanol and allowed to stand at room temperature to give additional pure product. Total yield was 0.038 g (60%):

IR (KBr) 1749, 1700, 1487, 1473 cm$^{-1}$.

$^1$H NMR (DMSO-d$_6$, 400 MHz) δ11.17 (s, 1H), 8.99 (dd, J=11.0, 9.1 Hz, 1H), 8.89 (dd, J=10.8, 8.6 Hz, 1H), 8.37 (dd, J=12.6, 7.2 Hz, 1H), 8.10 (dd, J=11.6, 6.8 Hz, 1H), 6.17 (br s, 1H), 5.95 (d, J=7.9 Hz, 1H), 5.57 (d, J=4.6 Hz, 1H), 5.53 (d, J=4.6 Hz, 1H), 4.89 (m, 1H), 4.57 (m, 1H), 4.41 (br m, 1H), 4.30 (dd, J=12.2, 2.9 Hz, 1H), 3.76 (d, J=5.7 Hz, 1H), 3.68 (m, 1H).

MS (ESI$^-$) m/e 540 (M–H)$^-$.

HPLC: 97.2% (320 nm).

EXAMPLE 4

2,3,9,10-Tetrafluoro-12,13-[1,6-(4-deoxy-β-D-glucopyranosyl)]-6,7,12,13-tetrahydro(5H)indolo[2,3-a]pyrrolo[3,4-c]carbazole-5,7-dione

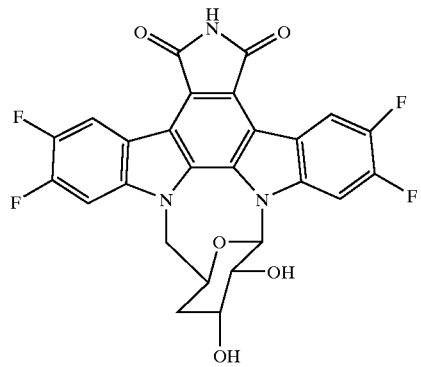

Prepared as per Example 3 as a yellow solid in 69% yield:

IR (KBr) 1717, 1700, 1487, 1473 cm$^{-1}$.

$^1$H NMR (DMSO-d$_6$, 400 MHz) δ9.19 (m, 1H), 9.09 (m, 1H), 8.37 (dd, J=12.5, 7.1 Hz, 1H), 7.69 (dd, J=11.2, 6.6 Hz, 1H), 5.90 (d, J=7.5 Hz, 1H), 4.64 (m, 3H), 4.48 (br s, 1H), 3.96 (dt, J=9.6, 8.6 Hz, 1H), 2.84 (dt, J=13.4, 8.5, 1H).

MS (ESI$^-$) m/e 524 (M–H)$^-$.

HPLC: 99.6% (320 nm).

EXAMPLE 5

2,3,9,10-Tetrafluoro-12,13-[1,6-(3-deoxy-β-D-glucopyranosyl)]-6,7,12,13-tetrahydro(5H)indolo[2,3-a]pyrrolo[3,4-c]carbazole-5,7-dione

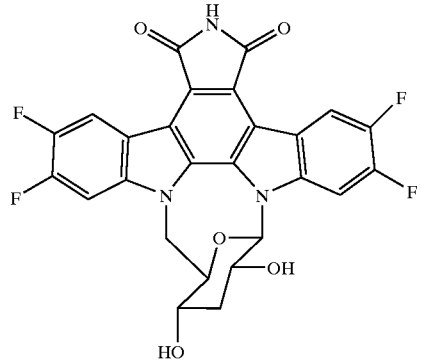

Prepared as per Example 3 as a yellow solid in 75% yield:

$^1$H NMR (acetone-d$_6$, 400 MHz) δ9.35 (s, 1H), 8.63 (m, 1H), 8.56 (m, 1H), 7.95 (m, 1H), 7.51 (m, 1H), 5.52 (d, J=5.6 Hz, 1H), 5.20 (br s, 1H), 4.45 (m, 3H), 4.18 (d, J=12.7 Hz, 1H), 4.07 (m, 1H), 3.91 (m, 1H), 2.50 (m, 1H), 1.84 (m, 1H).

MS (ESI$^-$) m/e 524 (M–H)$^-$.

HPLC: 98.5% (320 nm).

EXAMPLE 6
2,3,9,10-Tetrafluoro-12,13-[1,6-(3-deoxy-3-fluoro-β-D-glucopyranosyl)]-6,7,12,13-tetrahydro(5H)indolo[2,3-a]pyrrolo[3,4-c]carbazole-5,7-dione

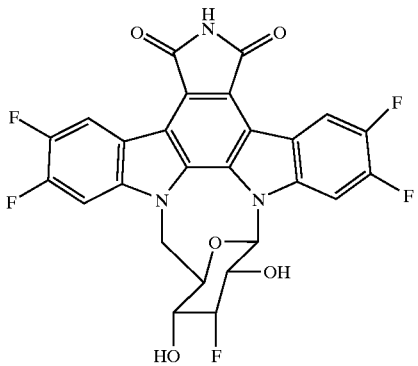

Prepared as per Example 3 as a yellow solid in 58% yield:
IR (KBr) 1826, 1757, 1489, 1475 cm⁻¹.
¹H NMR (THF-d₈, 400 MHz) δ10.83 (s, 1H), 8.92–8.80 (m, 2H), 8.48 (m, 1H), 7.88 (m, 1H), 6.38 (br s, 1H), 6.16 (d, J=7.8 Hz, 1H), 5.47 (br s, 1H), 4.96 (m, 2H), 4.84–4.67 (m, 2H), 4.56 (d, J=12.5 Hz, 1H), 4.15 (dt, J=25.0, 5.5 Hz, 1H
MS (ESI⁻) m/e 542 (M–H)⁻.
HPLC: 98.5% (320 nm).

EXAMPLE 7
1,11-Dichloro-12,13-[1,6-(4-O-methyl-β-D-glucopyranosyl)]-6,7,12,13-tetrahydro(5H)indolo[2,3-a]pyrrolo[3,4-c]carbazole-5,7-dione

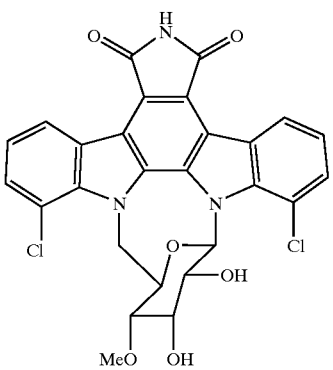

To a suspension of 1,11-dichloro-12-(4-O-methyl-β-D-glucopyranosyl)]-6,7,12,13-tetrahydro(5H)indolo[2,3-a]pyrrolo[3,4-c]carbazole-5,7-dione (0.184 g, 0.32 mmol) in 10 mL of THF, at room temperature under Ar, was added triphenylphosphine (0.262 g, 1.0 mmol) followed by diisopropyl azodicarboxylate (DIAD) (0.193 mL, 1.0 mmol). The resulting mixture was stirred at room temperature for 3 days and then it was filtered and the filtrate was evaporated to give a yellow gum. This gum was triturated with dichloromethane and the mixture was filtered to give a solid which was taken up in methanol and vigorously stirred, whereupon a solid separated. The solid was isolated by filtration and dried in vacuo to give the title compound (0.113 g, 64%) as a bright yellow solid:
IR (KBr) 1711, 1321, 1064 cm⁻¹.
¹H NMR (DMSO-d₆, 400 MHz) δ11.44 (s, 1H), 9.26 (d, J=7.9 Hz, 1H), 9.15 (d, J=7.9 Hz, 1H), 7.76 (d, J=7.4 Hz, 1H), 7.61 (d, J=7.8 Hz, 1H), 7.50 (t, J=7.9 Hz, 1H), 7.41 (t, J=7.9 Hz, 1H), 6.61 (d, J=7.3 Hz, 1H), 5.70 (dd, J=16.8, 5.8 Hz, 1H), 5.15 (d, J=5.9 Hz, 1H), 4.91 (d, J=6.0 Hz, 1H), 4.80 (d, J=5.6 Hz, 1H), 4.23 (d, J=5.0 Hz, 1H), 4.21 (d, J=16.1 Hz, 1H), 3.58 (s, 3H), 3.54 (m, 1H), 3.44 (m, 1H).
MS (ESI⁻) m/e 550 (M–H)⁻.
HPLC: 97.3% (320 nm).

EXAMPLE 8
2,3,9,10-Tetrafluoro-12,13-[1,6-(4-deoxy-4-fluoro-β-D-glucopyranosyl)]-6,7,12,13-tetrahydro(5H)indolo[2,3-a]pyrrolo[3,4-c]carbazole-5,7-dione

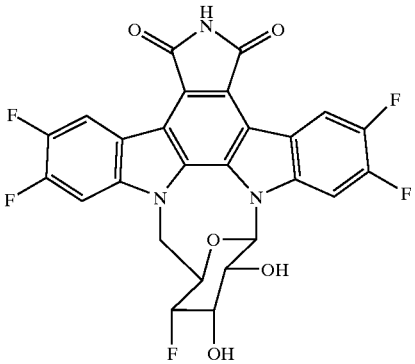

Prepared as per Example 7 as a yellow solid in 48% yield:
IR (KBr) 1750, 1700, 1488, 1473 cm⁻¹.
¹H NMR (THF-d₈, 400 MHz) δ10.06 (s, 1H), 9.17 (dd, J=11.3, 8.6 Hz, 1H), 9.07 (dd, J=11.1, 8.4 Hz, 1H), 8.36 (dd, J=12.3, 6.9 Hz, 1H), 7.79 (dd, J=11.3, 6.6 Hz, 1H), 6.04 (d, J=7.8 Hz, 1H), 5.93 (br s, 1H), 5.61 (br s, 1H), 4.87–4.50 (m, 5H), 4.10 (m, 1H).
MS (ESI⁻) m/e 542 (M–H)⁻.
HPLC: 99.0% (320 nm).

EXAMPLE 9
2,3,9,10-Tetrafluoro-12,13-[1,6-(4-deoxy-4,4-difluoro-β-D-glucopyranosyl)]-6,7,12,13-tetrahydro(5H)indolo[2,3-a]pyrrolo[3,4-c]carbazole-5,7-dione

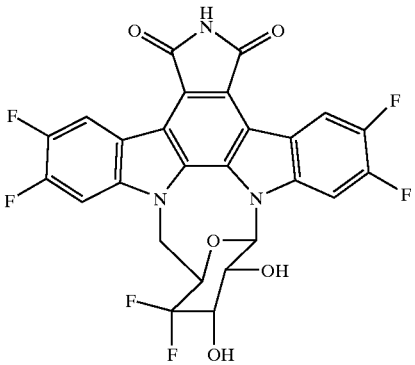

Prepared as per Example 7 as a yellow solid in 6% yield:
¹H NMR (acetone-d₆, 400 MHz) δ9.85 (s, 1H), 8.96 (dd, J=11.3, 8.7 Hz, 1H), 8.90 (dd, J=11.0, 8.5 Hz, 1H), 8.29 (dd, J=12.4, 7.1 Hz, 1H), 7.99 (dd, J=11.5, 6.7 Hz, 1H), 6.09 (d, J=8.0 Hz, 1H), 4.98–4.70 (m, 4H), 4.31 (dt, J=15.4, 11.3 Hz, 1H).
MS (ESI⁻) m/e 560 (M–H)⁻.
HPLC: 95.2% (320 nm).

EXAMPLE 10

2,10-Difluoro-12,13-[1,6-β-D-glucopyranosyl]-6,7,12,13-tetrahydro(5H)indolo-[2,3-a]pyrrolo[3,4-c]carbazole-5,7-dione

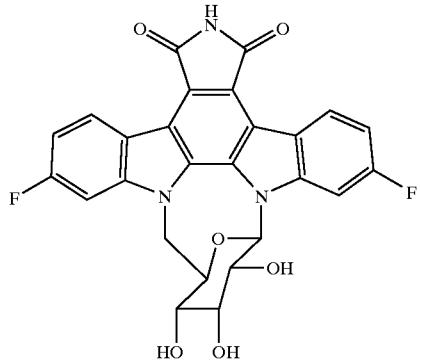

Prepared as per Example 7 in 12% yield as a yellow solid, mp >300° C.:

IR (KBr) 3414(br), 1744, 1702, 1619, 1582, 1490, 1468, 1449, 1415, 1328, 1182, 1112, 1043, 826, 763 cm$^{-1}$.

$^1$H NMR (DMSO-d$_6$, 500 MHz) δ9.22 (dd, J=8.6, 6.3 Hz, 1H), 9.14 (dd, J=8.6, 6.0 Hz, 1H), 8.14 (d, J=9.9 Hz, 1H), 7.81 (dd, J=10.5, 1.8 Hz, 1H), 7.24–7.18 (m, 2H), 5.98 (d, J=7.7 Hz, 1H), 5.63 (br s, 1.5H), 4.85–4.83 (m, 1H), 4.65–4.60 (m, 1H), 4.49 (m, 1H), 4.35–4.32 (m, 1H), 3.80 (d, J=6.3 Hz, 1H), 3.68 (dd, J=10.8, 6.3 Hz, 1H).

MS (ESI$^-$) m/e 504 (M−H)$^-$.

EXAMPLE 11

2,10-Difluoro-12,13-[1,6-(4-deoxy-4-fluoro-β-D-glucopyranosyl)]-6,7,12,13-tetrahydro(5H)indolo[2,3-a]pyrrolo[3,4-c]carbazole-5,7-dione

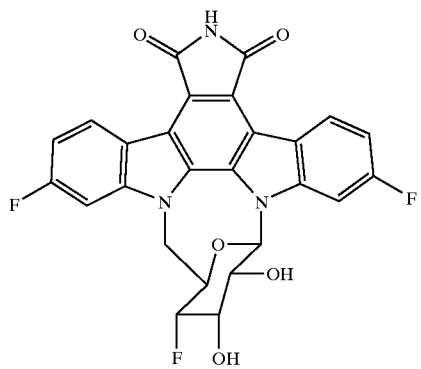

Prepared as per Example 7 and isolated in 24% yield after LH-20 chromatography (MeOH) as a yellow solid, mp 315° C. (dec):

IR (KBr) 3423, 2926, 1747, 1702, 1619, 1583, 1490, 1467, 1449, 1415, 1358, 1222, 1182, 1146, 1110, 1040, 996, 937, 827, 763, 641 cm$^{-1}$.

$^1$H NMR (DMSO-d$_6$, 500 MHz) δ9.21–9.19 (m, 1H), 9.12–9.10 (m, 1H), 8.10 (d, J=10.9 Hz, 1H), 7.92 (d, J=10.4 Hz, 1H), 7.21–7.15 (m, 2H), 6.08 (d, J=7.6 Hz, 1H), 5.04–5.01 (m, 1H), 4.87 (dd, J$_{HF}$=50.7, 5.3 Hz, 1H), 4.69–4.60 (2m, 2H), 4.55 (m, 1H), 3.98 (ddd, J$_{HF}$=28.0, J=10.8, 5.4 Hz, 1H).

MS (ESI$^-$) m/e 506 (M−H)$^-$.

EXAMPLE 12

2,3,9,10-Tetrafluoro-12,13-[1,4-(2,3,6-tri-O-benzyl-β-D-galactopyranosyl)]-6,7,12,13-tetrahydro(5H)indolo[2,3-a]pyrrolo[3,4-c]carbazole-5,7-dione

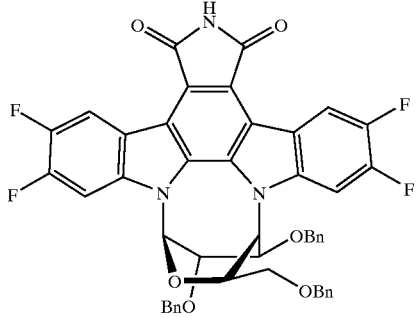

To a solution of 2,3,9,10-tetrafluoro-12-(2,3,6-tri-O-benzyl-β-D-glucopyranosyl)-6,7,12,13-tetrahydro(5H)indolo[2,3-a]pyrrolo[3,4-c]carbazole-5,7-dione (0.168 g, 0.20 mmol) and triphenylphosphine (0.157 g, 0.60 mmol) in 5 mL of dry benzene was added diisopropyl azodicarboxylate (DIAD) (0.118 mL, 0.60 mmol) dropwise at room temperature under Ar. After stirring at room temperature for 15 min, the resulting blood-red mixture was heated to reflux for 30 min. The cooled mixture was evaporated and the resulting orange gum was chromatographed (SiO$_2$/dichloromethane-acetonitrile, 1:0 then 97:3) to give the title compound (0.124 g, 77%) as a bright yellow glass:

$^1$H NMR (CDCl$_3$, 400 MHz) δ9.17 (dd, J=10.7, 8.3, 1H), 9.00 (dd, J=10.6, 8.2 Hz, 1H), 7.65 (br s, 1H), 7.48–7.30 (m, 9H), 7.20 (m, 3H), 7.13 (dd, J=7.6, 7.2 Hz, 2H), 6.67 (d, J=7.3 Hz, 2H), 6.61 (m, 1H), 6.33 (s, 1H), 5.52 (dd, J=8.5, 2.0 Hz, 1H), 4.84 (d, J=12.2 Hz, 1H), 4.83 (m, 1H), 4.54 (d, J=12.2 Hz, 1H), 4.34 (d, J=8.4 Hz, 1H), 4.31 (d, J=11.2 Hz, 1H), 4.04 (m, 2H), 3.95 (d, J=1.4 Hz, 1H), 3.56 (dd, J=8.9, 4.7 Hz, 1H), 3.02 (t, J=9.2 Hz, 1H).

MS (ESI$^-$) m/e 810 (M−H)$^-$.

EXAMPLE 13

2,3,9,10-Tetrafluoro-12,13-(1,4-β-D-galactopyranosyl)-6,7,12,13-tetrahydro(5H)indolo[2,3-a]pyrrolo[3,4-c]carbazole-5,7-dione

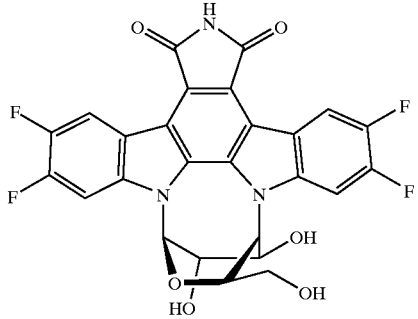

A mixture of 2,3,9,10-tetrafluoro-12,13-[1,4-(2,3,6-tri-O-benzyl-β-D-galactopyranosyl)]-6,7,12,13-tetrahydro(5H)indolo[2,3-a]pyrrolo[3,4-c]carbazole-5,7-dione (0.059 g, 0.073 mmol) and 20% Pd(OH)$_2$/C (0.059 g) in 10 mL of chloroform-methanol (1:1) was hydrogenated (balloon pressure) at room temperature with vigorous stirring for 17 h. The resulting mixture was then filtered (Celite) and the cake was washed successively with THF, methanol and dichloromethane. Evaporation of the filtrate gave a solid which was taken up in THF and filtered. The filtrate was evaporated and the residue was triturated with a minimum volume of cold methanol, filtered and dried in vacuo. This afforded the title compound (0.032 g, 80%) as a bright yellow solid:

IR (KBr) 1750, 1700, 1487, 1473 cm $^{-1}$.

$^1$H NMR (THF-d$_8$, 400 MHz) δ10.13 (br s, 1H), 9.20 (m, 2H), 7.79 (dd, J=12.0, 6.6 Hz, 1H), 7.71 (dd, J=11.4, 6.5 Hz, 1H), 6.56 (s, 1H), 5.71 (dd, J=7.9, 2.8 Hz, 1H), 5.46 (d, J=4.0 Hz, 1H), 4.76 (m, 1H), 4.63 (d, J=4.5 Hz, 1H), 4.46 (m, 1H), 4.12 (dd, J=5.6, 3.6 Hz, 1H), 4.05 (m, 1H), 3.43 (m, 1H), 2.97 (m, 1H).

MS (ESI$^-$) m/e 540 (M−H)$^-$.

HPLC: 95.5% (320 nm).

EXAMPLE 14

2,3,9,10-Tetrafluoro-12,13-[1,4-(2,3-di-O-benzyl-β-D-galactopyranosyl)]-6,7,12,13-tetrahydro(5H)indolo[2,3-a]pyrrolo[3,4-c]carbazole-5,7-dione

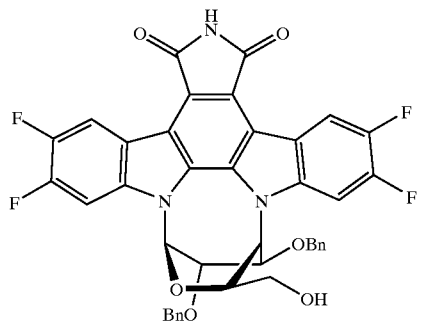

A mixture of 2,3,9,10-tetrafluoro-12,13-[1,4-(2,3-di-O-benzyl-β-D-galactopyranosyl)]-6,7,12,13-tetrahydro(5H)indolo[2,3-a]pyrrolo[3,4-c]carbazole-5,7-dione (0.124 g, 0.15 mmol) and iodine (0.010 mg, 0.038 mmol) in 5 mL of acetic anhydride was stirred at room temperature under Ar for 16 h. The resulting mixture was then evaporated in vacuo and the residue was taken up in toluene and again evaporated to give a yellow gum. This material was then taken up in 15 mL of methanol, 3 mL of ammonium hydroxide solution was added, the flask was sealed and the mixture was stirred at room temperature for 20 h. The mixture was then evaporated in vacuo and the residue was taken up in toluene and again evaporated to give a yellow gum. Flash chromatography of this material (SiO$_2$/dichloromethane-ethyl acetate, 9:1) afforded the title compound (0.078 g, 72%) as a yellow glass:

$^1$H NMR (CDCl$_3$, 400 MHz) δ8.81 (m, 1H), 8.65 (m, 1H), 7.85 (s, 1H), 7.38 (m, 6H), 7.22–7.14 (m, 3H), 6.78 (d, J=6.9 Hz, 2H), 6.54 (dd, J=10.4, 6.3 Hz, 1H), 6.29 (s, 1H), 5.47 (d, J=7.9 Hz, 1H), 4.81 (d, J=12.2 Hz, 1H), 4.75 (m, 1H), 4.52 (d, J=12.3 Hz, 1H), 4.36 (d, J=7.7 Hz, 1H), 4.15 (m, 2H), 3.96 (s, 1H), 3.67 (dd, J=10.8, 5.5 Hz, 1H), 3.39 (dd, J=10.6, 8.1 Hz, 1H), 2.06 (br s, 1H).

MS (ESI$^-$) m/e 720 (M−H)$^-$.

EXAMPLE 15

2,3,9,10-Tetrafluoro-12,13-[1,4-(6-deoxy-6-fluoro-2,3-di-O-benzyl-β-D-galactopyranosyl)]-6,7,12,13-tetrahydro(5H)indolo[2,3-a]pyrrolo[3,4-c]carbazole-5,7-dione

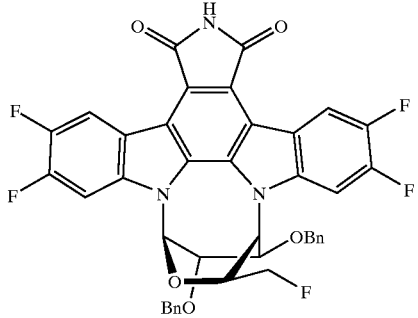

To a solution of 2,3,9,10-tetrafluoro-12,13-[1,4-(2,3-di-O-benzyl-β-D-galactopyranosyl)-6,7,12,13-tetrahydro(5H)indolo[2,3-a]pyrrolo[3,4-c]carbazole-5,7-dione (0.232 g, 0.32 mmol) in 7.5 mL of dry dichloromethane was added (diethylamino)sulfur trifluoride (DAST) (0.127 mL, 0.96 mmol) dropwise at −40° C. under Ar. After 20 min the cooling bath was removed and the mixture was stirred at room temperature for 3 h. The reaction mixture was then recooled at −40° C. and DAST (0.065 mL, 0.49 mmol) was again added. The mixture was then stirred at room temperature for 3 h, recooled at −40° C., quenched with methanol (10 mL) and evaporated to give a gum. Flash chromatography (SiO$_2$/dichloromethane-ethyl acetate, 1:0 then 95:5) of this material afforded the title compound (0.168 g, 72%) as a bright yellow glass:

$^1$H NMR (CDCl$_3$, 400 MHz) δ9.13 (dd, J=10.7, 8.3 Hz, 1H), 8.93 (dd, J=10.7, 8.2 Hz, 1H), 7.71 (s, 1H), 7.48 (m, 6H), 7.33 (dd, J=10.7, 6.2 Hz, 1H), 7.22 (t, J=7.3 Hz, 1H), 7.16 (dd, J=7.6, 7.1 Hz, 2H), 6.68 (d, J=7.1 Hz, 2H), 6.54 (dd, J=10.5, 6.3 Hz, 1H), 6.33 (s, 1H), 5.45 (d, J=8.6 Hz, 1H), 4.94 (m, 1H), 4.89 (d, J=12.2 Hz, 1H), 4.58 (d, J=12.3 Hz, 1H), 4.50 (dd, J=9.2, 5.2 Hz, 0.5H), 4.39 (d, J=8.2 Hz, 1H), 4.38 (m, 0.5H), 4.05 (m, 1H), 3.98 (m, 1H).

MS (ESI$^-$) m/e 722 (M−H)$^-$.

EXAMPLE 16

2,3,9,10-Tetrafluoro-12,13-[1,4-(6-deoxy-6-fluoro-β-D-galactopyranosyl)]-6,7,12,13-tetrahydro(5H)indolo[2,3-a]pyrrolo[3,4-c]carbazole-5,7-dione

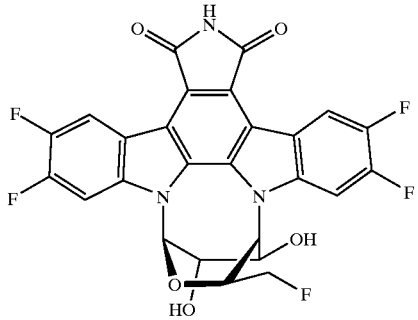

A mixture of 2,3,9,10-tetrafluoro-12,13-[1,4-(2,3-di-O-benzyl-6-deoxy-6-fluoro-β-D-galactopyranosyl)-6,7,12,13-tetrahydro(5H)indolo[2,3-a]pyrrolo[3,4-c]carbazole-5,7-dione (0.168 g, 0.23 mmol) and 20% Pd(OH)$_2$/C (0.185 g) in 25 mL of chloroform-methanol (1:1) was hydrogenated (balloon pressure) at r.t. with vigorous stirring for 3 days.

The resulting mixture was then filtered (Celite) and the cake was washed with methanol and then THF, and the filtrate was evaporated to give a solid. This material was chromatographed (SiO$_2$/dichloromethane-methanol-THF, 8:1:1) and the product-containing fractions were combined and rechromatographed (SiO$_2$/dichloromethane-methanol-THF, 90:5:5) to give the pure title compound (0.096 g, 77%) as a bright yellow solid:

IR (KBr) 17530, 1716, 1487, 1474 cm$^{-1}$.

$^1$H NMR (acetone-d$_6$, 400 MHz) δ9.22 (dd, J=11.2, 8.5 Hz, 1H), 9.18 (dd, J=11.3, 8.4 Hz, 1H), 7.90 (dd, J=11.7, 6.6 Hz, 1H), 7.87 (dd, J=11.8, 6.5 Hz, 1H), 6.77 (s, 1H), 5.96 (dd, J=8.6, 2.8 Hz, 1H), 5.10 (m, 1H), 4.70 (dd, J=6.5, 1.5 Hz, 1H), 4.40 (dd, J=10.0, 5.3 Hz, 0.5H), 4.30 (m, 1H), 4.19 (dd, J=9.7, 6.4 Hz, 0.5H), 3.29 (s, 1H).

MS (ESI$^-$) m/e 542 (M−H)$^-$.

HPLC: 97.5% (320 nm).

EXAMPLE 17

2,3,9,10-Tetrafluoro-12-(2,3-di-O-benzyl-4,6-dideoxy-5,6-anhydro-β-D-glucopyranosyl)-6,7,12,13-tetrahydro(5H)indolo[2,3-a]pyrrolo[3,4-c]carbazole-5,7-dione

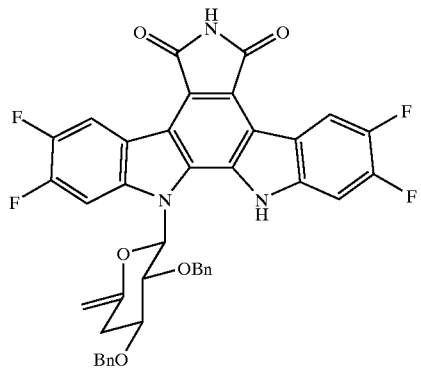

A mixture of 2,3,9,10-tetrafluoro-12-(2,3-di-O-benzyl-4-deoxy-β-D-glucopyranosyl)-6,7,12,13-tetrahydro(5H)indolo[2,3-a]pyrrolo[3,4-c]carbazole-5,7-dione (2.00 g, 2.76 mmol) and freshly activated, pulverized 4A molecular sieves (0.60 g) in 100 mL of dichloromethane was cooled at 5° C. under Ar and triethylamine (0.77 mL, 5.52 mmol), DMAP (0.20 g, 1.64 mmol) and methanesulfonyl chloride (0.32 mL, 4.14 mmol) were added sequentially. The mixture was stirred at the same temperature for 2 h and then it was filtered and the filter-cake was washed with ethyl acetate. The filtrate was diluted with ethyl acetate (200 mL) and ether (50 mL) and then it was washed (H$_2$O ×2, brine), dried (MgSO$_4$) and evaporated to give a yellow glass. This material was taken up in 100 mL of acetone, NaI ( ) was added and the mixture was heated to reflux under Ar for 18 h. The cooled mixture was then evaporated to dryness and the residue was taken up in 10 mL of ethyl acetate, washed (H$_2$O ×2, brine) dried (MgSO$_4$) and evaporated. The resulting solid was chromatographed (SiO$_2$/2–32% ethyl acetate-hexane) to give 2,3,9,10-tetrafluoro-12-(2,3-di-O-benzyl-4-deoxy-6-iodo-β-D-glucopyranosyl)-6,7,12,13-tetrahydro(5H)indolo[2,3-a]pyrrolo[3,4-c]carbazole-5,7-dione (0.90 g, 39%) as an amorphous yellow solid. To an ice-cold solution of this iodide (0.500 g, 0.60 mmol) in 20 mL of dry THF was added DBU (0.27 mL, 1.80 mmol) and the solution was kept at 5° C. for 2 h. The cooling bath was then removed and stirring was continued at room temperature for 16 h. Another portion of DBU (0.27 mL, 1.80 mmol) was then added and the reaction was allowed to continue for another 24 h. A further portion of DBU (0.27 mL, 1.80 mmol) was added and stirring was continued for an additional 24 h. The resulting mixture was diluted with ethyl acetate and then it was washed (1 N HCl ×2, H$_2$O ×2, 1 M NaHCO$_3$ ×2, H$_2$O, brine), dried (MgSO$_4$) and evaporated to give a gum. Flash chromatography (SiO$_2$/2–16% ethyl acetate-hexane) afforded the title compound (0.297 g, 70%) as a yellow solid:

$^1$H NMR (acetone-d$_6$, 400 MHz) δ9.11 (dd, J=11.0, 8.5 Hz, 1H), 8.95 (dd, J=11.0, 8.5 Hz, 1H), 7.94 (m, 1H), 7.46 (m, 2H), 7.37 (m, 4H), 6.84 (t, J=7.3 Hz, 1H), 6.69 (m, 2H), 6.57 (d, J=8.5 Hz, 1H), 6.43 (br s, 2H), 4.92 (d, J=11.4 Hz, 1H), 4.74(d, J=11.4 Hz, 1H), 4.69 (s, 1H), 4.58 (s, 1H), 4.40 (d, J=11.8 Hz, 1H), 4.26 (d, J=5.5 Hz, 2H), 3.99 (d, J=11.8 Hz, 1H), 3.25 (m, 1H).

MS (ESI$^-$) m/e 704 (M−H)$^-$.

EXAMPLE 18

2,3,9,10-Tetrafluoro-12-(2,3,4-tri-O-benzyl-6-deoxy-5,6-anhydro-β-D-glucopyranosyl)-6,7,12,13-tetrahydro(5H)indolo[2,3-a]pyrrolo[3,4-c]carbazole-5,7-dione

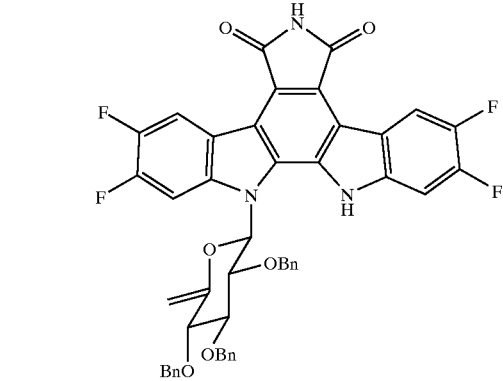

Prepared as per Example 17 as a yellow solid in 54% overall yield:

$^1$H NMR (CDCl$_3$, 400 MHz) δ9.38 (s, 1H), 9.13 (t, J=9.3 Hz, 1H), 8.99 (t, J=9.3 Hz, 1H), 7.56–7.41 (m, 6H), 7.29 (m, 2H), 6.90 (t, J=7.1 Hz, 1H), 6.74 (t, J=7.5 Hz, 2H), 6.68 (d, J=7.9 Hz, 1H), 6.43 (d, J=7.2 Hz, 3H), 5.06 (m, 2H), 4.84 (d, J=11.6 Hz, 1H), 4.74 (d, J=1.3 Hz, 1H), 4.68 (d, J=10.1 Hz, 1H), 4.58–4.54 (m, 2H), 4.19 (m, 1H), 3.94 (d, J=11.4 Hz, 1H).

MS (ESI$^-$) m/e 810 (M−H)$^-$.

EXAMPLE 19

2,3,9,10-Tetrafluoro-12,13-[1,5-(6-deoxy-6-iodo-2,3,4-tri-O-benzyl-β-D-glucopyranosyl]-6,7,12,13-tetrahydro(5H)indolo[2,3-a]pyrrolo[3,4-c]carbazole-5,7-dione

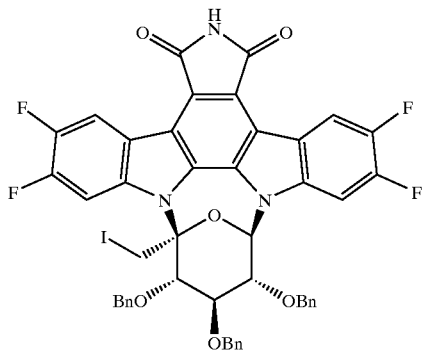

To a solution of 2,3,9,10-tetrafluoro-12-(2,3,4-tri-O-benzyl-6-deoxy-5,6-anhydro-β-D-glucopyranosyl)-6,7,12,13-tetrahydro(5H)indolo[2,3-a]pyrrolo[3,4-c]carbazole-5,7-dione (0.047 g, 0.058 mmol) in a mixture of THF (7 mL) and methanol (1 mL) was added potassium tert-butoxide (0.025 g, 0.22 mmol), followed by iodine (0.047 g, 0.19 mmol). The resulting brown mixture was stirred at room temperature under Ar for 18 h and then it was diluted with ethyl acetate. This mixture was then washed (aq. $NaS_2O_3$, brine), dried ($Na_2SO_4$) and evaporated to give a brown residue. Purification by prep tlc (hexane-ethyl acetate, 2:1) afforded the title compound (0.022 g, 41%) as a yellow solid:

$^1$H NMR ($CDCl_3$, 400 MHz) δ9.01 (dd, J=10.4 Hz, 8.6 Hz, 1H), 8.82 (dd, J=10.5 Hz, 8.2 Hz, 1H), 7.70 (s, 1H), 7.49 (m, 3H), 7.39 (d, J=3.6 Hz, 2H), 7.22–7.05 (m, 6H), 6.90–6.84 (m, 3H), 6.78 (d, J=7.3 Hz, 2H), 6.33 (dd, J=10.6 Hz, 6.2 Hz, 1H), 6.22 (d, J=4.9 Hz, 1H), 5.05 (d, J=11.9 Hz, 1H), 4.69 (t, J=11.1 Hz, 2H), 4.57–4.53 (m, 2H), 4.41 (d, J=11.1 Hz, 1H), 4.21 (d, J=11.6 Hz, 1H), 4.16–4.11 (m, 1H), 4.08 (m, 3H).

MS (ESI$^-$) m/e 936 (M−H)$^-$.

EXAMPLE 20

2,3,9,10-Tetrafluoro-12,13-[1,5-(4,6-dideoxy-6-iodo-2,3,4-tri-O-benzyl-β-D-glucopyranosyl)]-6,7,12,13-tetrahydro(5H)indolo[2,3-a]pyrrolo[3,4-c]carbazole-5,7-dione

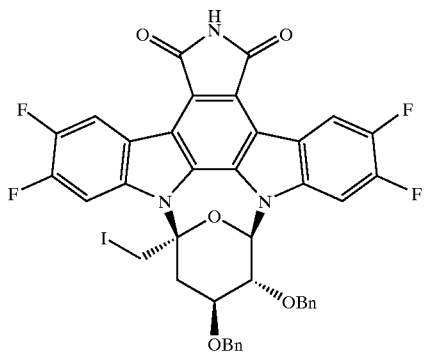

Prepared as per Example 19 in 68% yield.

$^1$H NMR (acetone-$d_6$, 500 MHz) δ9.10 (dd, J=10.4 Hz, 8.6 Hz, 1H), 8.95 (dd, J=10.4 Hz, 8.6 Hz, 1H), 8.02 (m, 1H), 7.6–7.4 (m, 7H), 7.08 (m, 1H), 6.90 (m, 1H), 6.76–6.65 (m, 2H), 6.70 (d, J=1 Hz, 1H), 5.05 (d, J=11.5 Hz, 1H), 4.98 (d, J=11.5 Hz, 1H), 4.91 (d, J=12.3 Hz, 1H), 4.23 (dd, J=3.3, 3.3 Hz, 1H), 4.22 (d, J=12.3 Hz, 1H), 4.15 (dd, J=1, 3.3 Hz, 1H), 3.80 (d, J=11.5 Hz, 1H), 3.73 (d, J=11.5 Hz, 1H), 3.25 (dd, J=3.3, 14.9 Hz, 1H), 3.01 (dd, J=3.3, 14.9 Hz, 1H).

MS (ESI$^-$) m/e 830 (M−H)$^-$.

EXAMPLE 21

2,3,9,10-Tetrafluoro-12,13-1,5-(6-deoxy-β-D-glucopyranosyl)]-6,7,12,13-tetrahydro(5H)indolo[2,3-a]pyrrolo[3,4-c]carbazole-5,7-dione

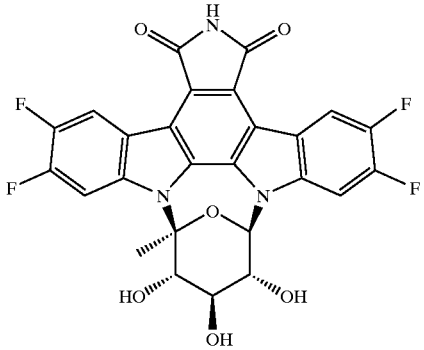

To a solution of 2,3,9,10-tetrafluoro-12,13-[1,5-(6-deoxy-6-iodo-2,3,4-tri-O-benzyl-β-D-glucopyranosyl)]-6,7,12,13-tetrahydro(5H)indolo[2,3-a]pyrrolo[3,4-c]carbazole-5,7-dione (0.025 g, 0.027 mmol) in 5 mL of dichloromethane, at −78° C. under Ar, was added a solution of boron tribromide (1 M in dichloromethane, 0.27 mL, 0.27 mmol) dropwise. After 30 min an additional 0.15 mL (0.15 mmol) of boron tribromide solution was added and the reaction mixture was allowed to warm to 0° C. over 1 h. The mixture was then recooled at −78° C., 0.20 mL (0.20 mmol) of boron tribromide solution was again added, and the mixture was allowed to warm to 0° C. over 2 h. The reaction mixture was then quenched with methanol, diluted with ethyl acetate, washed (brine), dried ($Na_2SO_4$) and evaporated. The residue was purified by prep tlc (THF-hexane, 2:1) to give the title compound (0.003 g, 21%) as a yellow solid:

$^1$H NMR (DMSO-$d_6$, 400 MHz) δ11.26 (s, 1H), 8.97 (t, J=9.5 Hz, 1H), 8.76 (t, J=9.1 Hz, 1H), 8.01–7.91 (m, 2H), 6.46 (d, J=5.2 Hz, 1H), 6.26 (d, J=5.3 Hz, 1H), 5.87 (d, J=5.3 Hz, 1H), 5.38 (s, 2H), 4.21 (m, 1H), 4.10 (m, 1H), 3.79–3.71 (m, 2H), 3.16 (d, J=5.3 Hz, 1H).

MS (ESI$^-$) m/e 540 (M−H)$^-$.

HPLC: 97.0% (320 nm).

EXAMPLE 22

2,3,9,10-Tetrafluoro-12,13-(1,5-β-D-glucopyranosyl)-6,7,12,13-tetrahydro(5H)indolo[2,3-a]pyrrolo[3,4-c]carbazole-5,7-dione

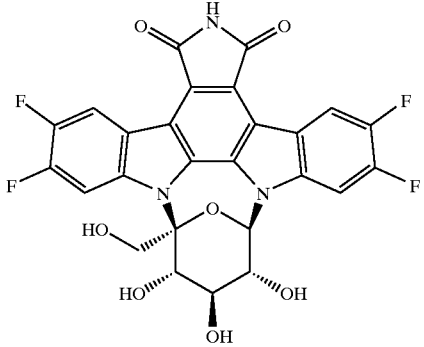

To a solution of 2,3,9,10-tetrafluoro-12,13-[1,5-(6-deoxy-6-iodo-2,3,4-tri-O-benzyl-β-D-glucopyranosyl)]-6,7,12,13-tetrahydro(5H)indolo[2,3-a]pyrrolo[3,4-c]carbazole-5,7-dione (0.025 g, 0.027 mmol) in 4 mL of dichloromethane containing several drops of water, was added m-chloroperbenzoic acid (0.018 g, 0.11 mmol) and the resulting mixture was stirred at room temperature for 3 days. The mixture was then partitioned with ethyl acetate and saturated aqueous NaHSO$_3$.and the organic phase was separated, washed (saturated aqueous NaHCO$_3$, brine), dried (NaSO$_4$) and evaporated to give a solid. Purification by prep tlc afforded 2,3,9,10-tetrafluoro-12,13-[1,5-(6-hydroxy-2,3,4-tri-O-benzyl-β-D-glucopyranosyl)]-6,7,12,13-tetrahydro(5H)indolo[2,3-a]pyrrolo[3,4-c]carbazole-5,7-dione (0.006 g, 27%) as a yellow solid: MS (ESI$^-$) m/e 826 (M−H)$^-$. This material was taken up in dichloromethane (5 mL), the solution was cooled at −78° C. under Ar and a solution of boron tribromide (1 M in dichloromethane, 0.073 mL, 0.073 mmol) was then added dropwise. The resulting mixture was kept at −78° C. for 15 min, then at 0° C. for 75 min and finally it was quenched with methanol and diluted with ethyl acetate. This mixture was then washed (brine), dried (Na$_2$SO$_4$) and evaporated, and the residue was purified by prep tlc (THF-hexane, 3:2) to give the title compound (0.0016 g, 40%) as a yellow solid:

$^1$H NMR (acetone-d$_6$, 400 MHz) δ10.01 (s, 1H), 9.09 (dd, J=11.4 Hz, 8.7 Hz, 1H), 8.88 (t, J=8.8 Hz, 1H), 7.88–7.76 (m, 2H), 6.55 (d, J=6.0 Hz, 1H), 4.79–4.67 (m, 2H), 4.26–4.18 (m, 2H), 4.12–4.06 (m, 1H), 3.89–3.78 (m, 2H), 3.52 (m, 1H), 3.29 (s, 1H).

MS (ESI$^-$) m/e 556 (M−H)$^-$.

HPLC: 98.1% (320 nm).

EXAMPLE 23

2,3,9,10-Tetrafluoro-12,13-[1,5-(6-deoxy-β-D-glucopyranosyl)]-6,7,12,13-tetrahydro(5H)indolo[2,3-a]pyrrolo[3,4-c]carbazole-5-one and 2,3,9,10-Tetrafluoro-12,13-[1,5-(6-deoxy-β-D-glucopyranosyl)]-6,7,12,13-tetrahydro(5H)-indolo[2,3-a]pyrrolo[3,4-c]carbazole-7-one

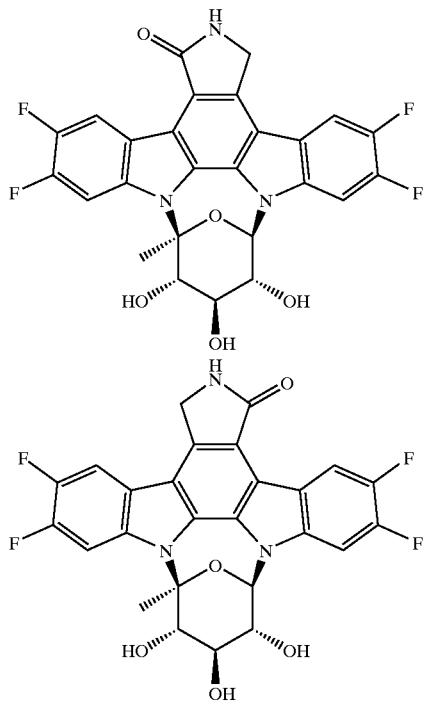

To a solution of 2,3,9,10-tetrafluoro-12,13-[1,5-(6-deoxy-2,3,4-tri-O-benzyl-β-D-glucopyranosyl)]-6,7,12,13-tetrahydro(5H)indolo[2,3-a]pyrrolo[3,4-c]carbazole-5,7-dione (0.060 g, 0.074 mmol) in 10 mL of ethanol was added sodium borohydride (0.027 g, 0.71 mmol) in three portions at 1 h intervals. One hour after the final addition, another 0.035 g (0.92 mmol) of sodium borohydride was added and the resulting mixture was stirred at room temperature for 3 days. The mixture was then diluted with ethyl acetate, washed (sat. NH$_4$Cl, sat. NaHCO$_3$, brine), dried (Na$_2$SO$_4$) and evaporated to give a solid residue. This residue was immediately taken up in dichloromethane (5 mL) and phenylselenol (0.055 mL, 0.52 mmol) was added, followed by p-toluenesulfonic acid monohydrate (0.003 g, 0.015 mmol). After 2 h at room temperature, the resulting mixture was evaporated and the residue was purified by prep tlc (dichloromethane-methanol, 97:3) to give a 1:1 mixture of 2,3,9,10-tetrafluoro-12,13-[1, 5-(6-deoxy-2,3,4-tri-O-benzyl-β-D-glucopyranosyl)]-6,7,12,13-tetrahydro(5H) indolo[2,3-a]pyrrolo[3,4-c]carbazole-5-one and 2,3,9,10-tetrafluoro-12,13-[1,5-(6-deoxy-2,3,4-tri-O-benzyl-β-D-glucopyranosyl)]-6,7,12,13-tetrahydro(5H)indolo[2,3-a]pyrrolo[3,4-c]carbazole-7-one (0.014 g, 24%) as a nearly colourless solid: MS (ESI$^-$) m/e 796 (M−H)$^-$. This material was taken up in dichloromethane (5 mL), cooled at −78° C. and then treated with boron tribromide (1 M in dichloromethane, 0.18 mL, 0.18 mmol). The mixture was stirred at −78° C. for 15 min and then at −20° C. for 2 h, before being recooled at −78° C. and again being treated with boron tribromide (1 M in dichloromethane, 0.10 mL, 0.10 mmol). The mixture was then kept at 5° C. for 18 h and at room temperature for an additional 5 h. This process was repeated once more and then the resulting mixture was partitioned with 1 N HCl and ethyl acetate. The organic phase was separated, washed (1 N HCl, brine), dried (Na$_2$SO$_4$) and evaporated, and the residue obtained was purified by prep tlc (THF-hexane, 2:1) to give an inseparable 1:1 mixture of the title compounds (0.0032 g, 36%) as a nearly colourless solid:

$^1$H NMR (acetone-d$_6$, 400 MHz) δ9.34 (dd, J=11.8 Hz, 9.0 Hz, 1H), 9.08 (dd, J=11.6 Hz, 8.6 Hz, 1H), 7.94 (dd, J=10.5 Hz, 7.9 Hz, 1H), 7.81–7.72 (m, 1H), 7.69–7.59 (m, 1H), 6.47 (dd, J=5.4 Hz, 3.2 Hz, 1H), 5.48–5.31 (m, 2H), 5.03–4.90 (m, 2H), 4.50–4.45 (m, 1H), 4.20–4.12 (m, 1H), 4.07–4.02 (m, 1H), 3.61 (m, 1H), 2.72 (s, 3H).

MS (ESI$^-$) m/e 526 (M−H)$^-$.

HPLC: 98.0% (320 nm).

EXAMPLE 24

2,10-Difluoro-12,13-[1,2-β-D-glucopyranosyl]-6,7,12,13-tetrahydro(5H)-indolo-[2,3-a]pyrrolo[3,4-c]carbazole-5,7-dione

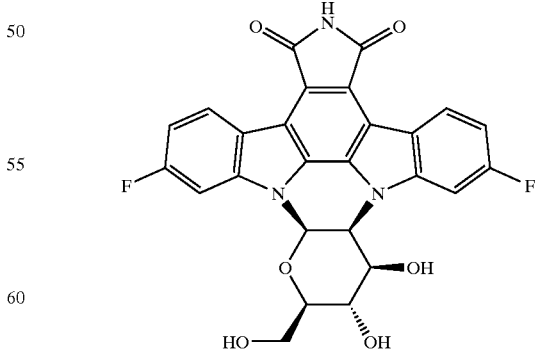

A mixture of 2,10-difluoro-12-(3,4,6-tri-O-benzyl-β-D-glucopyranosyl)-6,7,12,13-tetrahydro(5H)indolo[2,3-a]pyrrolo[3,4-c]carbazole-5,7-dione (0.100 g, 0.126 mmol) and flame-dried, powdered 4A molecular sieves (0.10 g) in dry pyridine (3 mL) was cooled to 0° C. under nitrogen for 15 min before methanesulfonyl chloride (0.012 mL, 0.15 mmol) was added. The mixture was stirred for 8 h at room temperature and then it was recooled to 0° C. and treated with additional methanesulfonyl chloride (0.015 mL). The mixture was then stirred at room temperature for 1 h. This sequence was repeated every hour until all of the starting material was consumed. The mixture was then diluted with ethyl acetate and washed with 0.1 N HCl, saturated NaHCO$_3$ and brine, prior to drying and solvent evaporation. Purification of the residue by flash chromatography (ethyl acetate-hexane, 3:7) afforded the mesylate (0.080 g, 73%) as a yellow solid which was used directly in the next step. The mesylate was taken up in anhydrous dimethylformamide (1 mL) and dry diisopropylethylamine (0.050 mL, 0.29 mmol) was added. The mixture was heated to 110° C. for 1 h and then was stirred at ambient temperature overnight. The resulting mixture was diluted with ethyl acetate and THF, washed with 1 N HCl and brine, dried and concentrated. The residue was taken up in EtOH-THF-MeOH (3:3:1), 10% palladium hydroxide-on-carbon (0.30 g) was added and the mixture was hydrogenated in a Parr shaker at room temperature and 60 psi for 24 h. The mixture was then filtered through Celite and the filtercake was washed with THF and methanol. The filtrate was concentrated in vacuo and the residue was purified by flash chromatography (chloroform-methanol, 9:1) to yield the title compound (0.020 g, 32% overall) as a yellow solid, mp >300° C.:

IR (KBr) 3307 (br), 2926, 2876, 1745, 1710, 1697, 1619, 1575, 1466, 1438, 1349, 1322, 1174, 1117, 1070, 1025, 760 cm$^{-1}$.

$^1$H NMR (DMSO-d$_6$, 500 MHz) δ11.09 (s, 1H), 8.81 (d, J=10.8 Hz, 1H), 8.73 (dd, J=8.3, 6.4 Hz, 1H), 8.61 (dd, J=8.4, 5.6 Hz, 1H), 7.87 (d, J=8.0 Hz, 1H), 7.34–7.27 (m, 2H), 6.84 (d, J=4.6 Hz, 1H), 6.80 (s, 1H), 5.64 (d, J=5.1 Hz, 1H), 5.15 (s, 1H), 4.40–4.33 (m, 2H), 3.70–3.68 (m, 1H), 3.59–3.58 (m, 1H), 3.5–3.48 (m, 1H), 3.37–3.25 (m, 1H). MS (ESI$^-$) m/e 504 (M–H)$^-$.

EXAMPLE 25

3,9-Difluoro-12,13-[1,2-β-D-galactopyranosyl]-6,7,12,13-tetrahydro(5H)-indolo-[2,3-a]pyrrolo[3,4-c]carbazole-5,7-dione

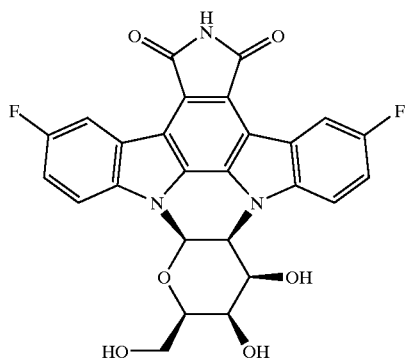

To a stirred solution of 3,9,-difluoro-6-(4-tert-butylbenzyl)-12-(4-deoxy-4-fluoro-β-D-glucopyranosyl)]-6,7,12,13-tetrahydro(5H)indolo[2,3-a]pyrrolo[3,4-c]carbazole-5,7-dione (2.22 g, 3.31 mmol) in absolute ethanol (750 mL) was added 4.45 M KOH (75 mL) and the resulting blood red solution was allowed to stir overnight at room temperature. The reaction was acidified with conc. HCl (80 mL), solid ammonium acetate (750 g, ) and absolute ethanol (350 mL) were added and the reaction mixture was refluxed for 5 days. The reaction mixture was then concentrated by approximately ⅔, cooled to room temperature and ethyl acetate (3500 mL) and water (1500 mL) were added. The organic layer was extracted with water (4×1500 mL), saturated sodium bicarbonate (1×1500 mL), water (1×1500 mL) and brine (1×1500 mL), dried over Na$_2$SO$_4$, filtered and the solvent removed in vacuo. The resulting residue was pre-adsorbed onto silica gel and applied to a flash column packed in methylene chloride and eluted with a methylene chloride-acetone gradient. Further purification on Sephadex LH-20 in methanol gave the 0.0237 g of the title compound (1.4%):

500 MHz COSY $^1$H NMR (d$_6$-DMSO) δ11.04 (brs, 1H), 8.32 (dd, 1H, J=9.1, 2.8 Hz), 8.22 (dd, 1H, J=9.1, 2.6 Hz), 8.06 (dd, 1H, J=9.0, 4.4 Hz), 7.93 (dd, 1H, J=9.3, 4.3 Hz), 7.45–7.35 (m, 2H), 6.72 (brs, 1H, 1'H), 6.13 (brs, 1H, 3'OH), 5.38 (brs, 1H, 3'H), 4.77 (brs, 1H, 2'H), 4.73 (d, 1H, 4'OH, J=5.5 Hz), 4.73 (t, 1H, 6'OH, J=5.4 Hz), 4.28 (dd, 1H, 5'H, J=6.2, 6.1 Hz), 3.71 (brs, 1H, 4'H), 3.38–3.18 (m, 2H, 6'H, 6"H); MS (ESI$^-$) m/e 504 (M–H)$^-$.

EXAMPLE 26

3,9-Difluoro-12,13-[1,6-(4-deoxy-4-fluoro-β-D-glucopyranosyl)]-6,7,12,13-tetrahydro(5H)indolo[2,3-a]pyrrolo[3,4-c]carbazole-5,7-dione

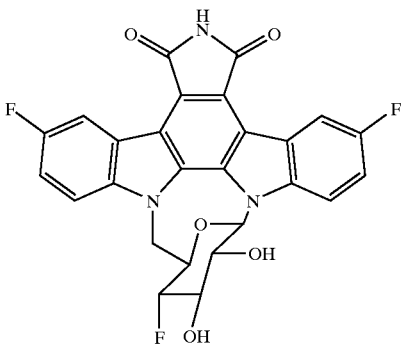

To a stirred solution of 3,9,-difluoro-12-(4-deoxy-4-fluoro-β-D-glucopyranosyl)]-6,7,12,13-tetrahydro(5H)indolo[2,3-a]pyrrolo[3,4-c]carbazole-5,7-dione (0.0100 g, 0.019 mmol) and triphenylphosphine (0.010 g, 0.038 mmol) in anhydrous THF (200 μL) was added diisopropyl azodicarboxylate (7.5 μL, 0.038 mmol). The resulting blood red solution was stirred at room temperature for 3 h, after which additional diisopropyl azodicarboxylate (3 μL, 0.015 mmol) was added. The reaction was stirred at room temperature for an additional 30 minutes, then quenched with methanol (1 mL) and the solvent removed in vacuo. Purification by flash column chromatography on silica gel using an acetone-hexane gradient, followed by purification on Sephadex LH-20 in methanol, gave 0.0041 g (42.5%) of the title compound:

500 MHz COSY $^1$H NMR (d$_6$-DMSO) δ8.97 (dd, 1H, J=9.7, 2.5 Hz), 8.88 dd, (1H, J=9.7, 2.5 Hz), 8.34 (dd, 1H, J=9.2, 4.5 Hz), 8.08 (dd, 1H, J=9.0, 4.2 Hz), 7.54–7.45 (m, 2H), 6.20 (d, 1H, 1'H, J=7.80 Hz), 5.11 (brd, 1H, 6'H, J=12 Hz), 4.91 (dd, 1H, 4'H, J$_{H-F}$=50.6 Hz, J$_{3',4'}$=5.4 Hz), 4.68 (brs, 1H, 5'H), 4.71–4.64 (m, 1H, 6"H), 4.60–4.45 (m, 1H, 2'H, J$_{2,3}$=5.6 Hz), 3.99 (brddd, 1H, 3'H, J$_{H-F}$=28 Hz, J$_{3,4}$=5.5 Hz, J$_{2,3}$=5.6 Hz); MS (ESI$^-$) m/e 506 (M–H)$^-$. Confirmed by X-ray crystallography.

EXAMPLE 27 AND 28

3,9-Difluoro-12,13-[1,6-β-D-glucopyranosyl)]-6,7,12,13-tetrahydro(5H)indolo[2,3-a]pyrrolo[3,4-c]carbazole-5,7- dione (1) and 3,9-Difluoro-12,13-[1,2-β-D-glucopyranosyl]-6,7,12,13-tetrahydro(5H)-indolo-[2,3-a]pyrrolo[3,4-c]carbazole-5,7-dione (2)

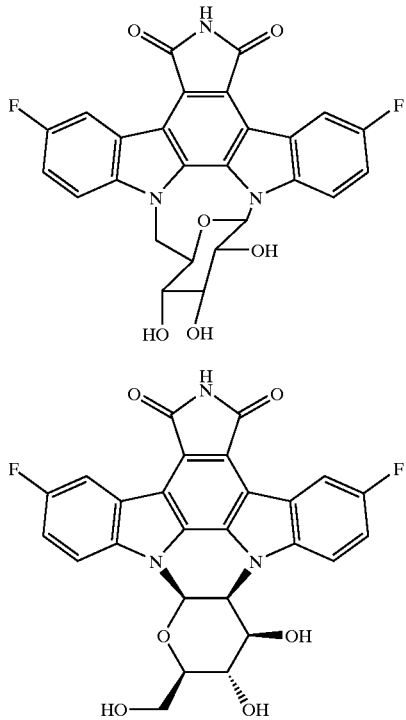

To a stirred solution of 3,9,-difluoro-12-β-D-glucopyranosyl-6,7,12,13-tetrahydro(5H)indolo[2,3-a]pyrrolo[3,4-c]carbazole-5,7-dione (0.240 g, 0.459 mmol) and triphenylphosphine (0.263 g, 1.00 mmol) in anhydrous THF (10 mL) was added diisoproply azodicarboxylate (200 μL, 1.01 mmol) and the resulting blood red solution was allowed to stir at room temperature for 2 h. The reaction was then quenched with water (5 drops) and the solvent removed in vacuo. Partial purification by flash column chromatography on silica gel (acetone-hexane) afforded 2 components which were individually repurified on Sephadex LH-20 (methanol) to give the 2 pure title compounds. The first was identified as 3,9-difluoro-12,13-[1,6-β-D-glucopyranosyl)]-6,7,12,13-tetrahydro(5H)indolo[2,3-a]pyrrolo[3,4-c]carbazole-5,7-dione (0.019 g, 8.2%):

500 MHz COSY $^1$H NMR (d$_6$-DMSO) δ8.87 (dd, 1H, J=9.8, 2.6 Hz), 8.79 (dd, 1H, J=9.7, 2.6), 8.30 (dd, 1H, J=9.1, 4.3 Hz), 7.88 (dd, 1H, J=9.1, 4.3 Hz), 7.52–7.39 (m, 2H), 6.03 (d, 1H, 1'-H, J=7.8 Hz), 5.60 (br s, 1H, 4'-OH), 5.50 (br s, 1H, 3'-OH), 4.81 (br d, 1H, 6'-H, J=12.0 Hz), 4.60 (dd, 1H, 6'-H, J=12.2 Hz), 4.40–4.28 (m, 2H, 2'-H, 5'-H), 3.78 (br d, 1H, 4'-H), 3.70–3.62 (m, 1H, 3'-H);

MS (ESI$^-$) m/e 504 (M–H)$^-$.

The second was identified as 3,9-difluoro-12,13-[1,2β-D-glucopyranosyl]-6,7,12,13-tetrahydro(5H)-indolo-[2,3-a]pyrrolo[3,4-c]carbazole-5,7-dione (0.019 g, 8.2%):

500 MHz COSY $^1$H NMR (d$_6$-DMSO) δ11.01 (br s, 1H), 8.84 (dd, 1H, J=9.4, 4.6 Hz), 8.32 (dd, 1H, J=9.0, 2.8 Hz), 8.20 (dd, 1H, J=9.1, 2.7 Hz), 7.89 (dd, 1H, J=9.0, 4.5 Hz), 7.42 (m, 1H), 7.35 (m, 1H), 6.72 (s, 1H, 1'-H), 6.57 (d, 1H, 3'-OH, J=4.80 Hz), 5.45 (d, 1H, 4'-OH, J=5.10 Hz), 5.06 (br s, 1H, 2'-H), 4.32–4.22 (m, 2H, 3'-H, 6'-H), 3.62–3.57 (m, 1H, 5'-H), 3.52–3.45 (m, 1H, 4'-H), 3.40 (d, 1H, 6'-H); MS (ESI$^-$) m/e 504 (M–H)$^-$.

Topoisomerase I Activity (In Vitro)

Topoisomerase I activity was measured as described below: The procedure for assaying compound-induced, topoisomerase I-mediated single strand breaks in DNA was essentially that described by Hsiang, et al., (*J. Biol Chem.* 1985, 260, 14873–14878). Samples dissolved in 100% DMSO as either 10 μM or 10 mg/ml solutions, unless otherwise stated, were diluted in Tris-EDTA buffer. Marine bacteriophage PM2 DNA (Boehringer Mannheim) was also diluted in Tris-EDTA buffer to a concentration of 0.02 μg/μl. Different dilutions of the compound being evaluated were mixed with diluted DNA and this mixture was added to 1000 unit (one unit of enzyme activity is defined as the amount capable of relaxing 100 ng of supercoiled DNA in approximately 30 minutes at 37° C.) aliquots of purified human topoisomerase I (Topogen) in 2× reaction buffer to start the reaction. The compound-DNA-enzyme mixture was incubated for 30 minutes at 37° C. before stopping the reaction with warm stop buffer containing sodium dodecyl sulfate and proteinase K (Sigma). These mixtures were allowed to incubate at 37° C. for another 10 minutes, at which time the mixtures were removed from the waterbath and extracted with a 24:1 mixture of chloroform/isoamyl alcohol. Following centrifugation, aliquots of the aqueous phases were placed in wells of a 0.9% agarose (SeaKem) gel in Tris-borate buffer containing 0.5 μg/ml of ethidium bromide and subjected to electrophoresis for 15 hours to separate the different topological isomers and nicked and broken DNAs. After destaining the gel in water, the ethidium bromide stained DNA reaction products were visualized by exposing the gel to UV irradiation. Negatives of the photographs of the irradiated gels were scanned with a densitometer and areas under the peaks were calculated in order to obtain percent single strand DNA break formation for each sample. A median effective concentration (EC$_{50}$) was obtained for each compound by interpolation between points of the resulting dose-effect curve which defines the potency of the compound for its effect in inducing topoisomerase I-mediated single strand breaks in DNA.

The topoisomerase I activity for certain compounds of the present invention is shown below in Table I.

TABLE I

| Example No. | EC$_{50}$ (μM) |
|---|---|
| 13 | 8.2 |
| 16 | 2.9 |
| 21 | 0.29 |
| 22 | 0.32 |
| 23 | 2.1 |
| 3 | 0.35 |

TABLE I-continued

| Example No. | EC$_{50}$ ($\mu$M) |
| --- | --- |
| 4 | 5.6 |
| 8 | 0.62 |
| 9 | >100 |
| 6 | >100 |
| 5 | 0.68 |
| 7 | >100 |
| 24 | >100 |
| 10 | 0.45 |
| 11 | 3.3 |
| 25 | 0.110 |
| 26 | 0.028 |
| 27 | 0.036 |
| 28 | 0.120 |

In Vitro Cell-Based Cytotoxicity Activity

The proliferation inhibition activity against murine P388 cell line was measured as follows. Evaluation of a soluble tetrazolium/formazan assay for cell growth and drug sensitivity in culture, using human and other tumor cell lines, was done according to the procedure described in *Cancer Res.* 1988, 48, 4827–4833. Cells were plated at 4000 cells/well in 96 well microtiter plates and 24 h later drugs were added and serially diluted. The cells were incubated at 37° C. for 72 h, at which time a tetrazolium dye, XTT, containing phenazine methosulfate was added. A dehydrogenase enzyme in live cells reduced the XTT to a form that absorbs light at 450 nm, which could be quantitated spectrophotometrically. The greater the absorbance the greater the number of live cells. The results are expressed as an IC$_{50}$, which is the drug concentration required to inhibit cell proliferation (i.e., absorbance at 450 nm) to 50% of that of untreated control cells. The results for certain compounds of the present invention are shown in Table II.

TABLE II

| Example No. | IC$_{50}$ ($\mu$M) |
| --- | --- |
| 13 | 2.8 |
| 16 | 3.3 |
| 21 | 0.14 |
| 22 | 0.086 |
| 23 | 0.24 |
| 3 | 0.05 |
| 4 | 0.07 |
| 8 | 0.026 |
| 9 | 0.021 |
| 6 | 7.7 |
| 5 | 0.023 |
| 7 | 0.46 |
| 24 | 1.15 |
| 10 | 0.13 |
| 11 | 0.021 |
| 25 | 0.0142 |
| 26 | 0.0030 |
| 27 | 0.0511 |
| 28 | 0.3468 |

What is claimed is:

1. A compound of Formula (I) or a pharmaceutically acceptable addition salt or solvate thereof,

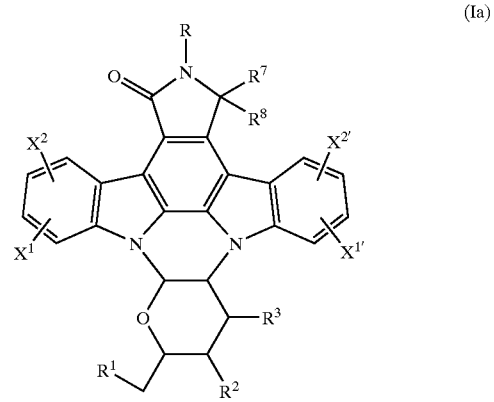

(Ia)

wherein:

R is hydrogen, OH, OC$_{1-7}$alkyl, NH$_2$, N(C$_{1-3}$alkyl)$_2$, or C$_{1-7}$alkyl, wherein said C$_{1-7}$alkyl or C$_{1-3}$alkyl is optionally substituted with one or more substituents selected from the group consisting of halogen, CN SR$^9$, OR$^9$ and NR$^9$R$^{10}$;

R$^1$, R$^2$ and R$^3$ are each independently selected from the group consisting of hydrogen, C$_{1-7}$alkenyl, C$_{3-7}$cycloalkyl, halogen, azido, NR$^9$R$^{10}$, NHC(O) NR$^9$R$^{10}$, NHC(O)OR$^9$, C(O)OR$^9$, SR$^9$ and OR$^9$, wherein said C$_{1-7}$alkenyl is optionally substituted with one or more substituents selected from the group consisting of halogen, CN, SR$^9$, OR$^9$ and NR$^9$R$^{10}$; provided that no more than two of the variables selected from the group consisting of R$^1$ R$^2$ and R$^3$ may be C$_{3-7}$cycloalkyl, azido, NHC(O)NR$^9$R$^{10}$ or NHC(O) OR$^9$;

R$^7$ and R$^8$ are independently OH or H or R$^7$ and R$^8$ together form =O;

R$^9$ and R$^{10}$ are independently selected from the group consisting of hydrogen, C$_{1-7}$alkyl and C$_{3-7}$cycloalkyl, wherein said C$_{1-7}$alkyl is optionally substituted with one or more substituents selected from the group consisting of halogen, CN, OH, O-C$_{1-7}$alkyl, NH$_2$ and N(C$_{1-3}$alkyl)$_2$; or R$^9$ and R$^{10}$ together with the nitrogen atom to which they are attached form a non-aromatic 5–8 membered heterocycle containing one or two of the same or different heteroatoms selected from the group consisting of O, N and S; and X$^1$, X$^{1'}$, X$^2$ and X$^{2'}$ are independently selected from the group consisting of hydrogen, halogen, cyano, OR$^9$, —CF$_3$, alkylcarbonyl, C$_{1-7}$alkyl, nitro, alkoxyaminoalkyl, NR$^9$R$^{10}$, SR$^9$ and C(O)OR$^9$; wherein said C$_{1-7}$alkyl is optionally substituted with one or more substituents selected from the group consisting of halogen, CN, OR$^9$, SR$^9$ and NR$^9$R$^{10}$, wherein at least one of X$^1$ and X$^2$ is F and at least one of X$^{1'}$ and X$^{2'}$ is F.

2. The compound of claim 1, wherein R$^7$ and R$^8$ together are =O.

3. The compound of claim 2, wherein one of X$^1$ and X$^2$ is F at either the 2- or the 3-position and the other is H, and one of X$^{1'}$ and X$^{2'}$ is F at either the 9- or the 10-position, and the other is H.

4. The compound of claim 3, wherein the compound of Formula (I) is:
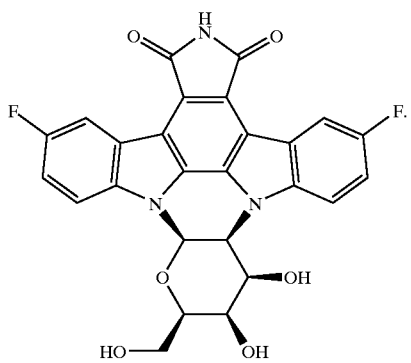
5. A compound selected from the group consisting of:
a.
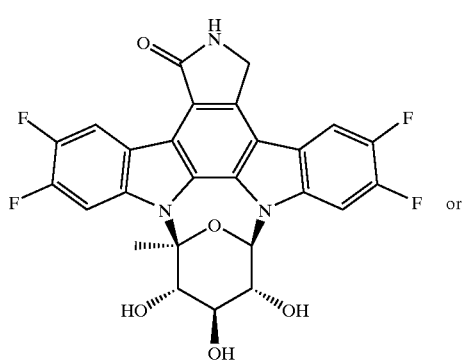
or
b.
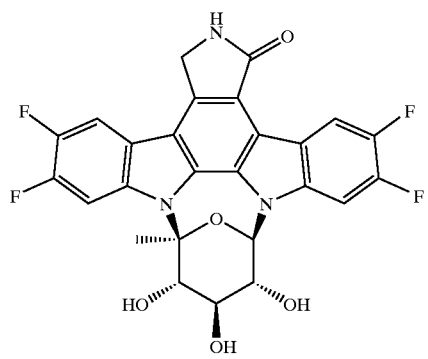
6. A compound selected from the group consisting of:
a.
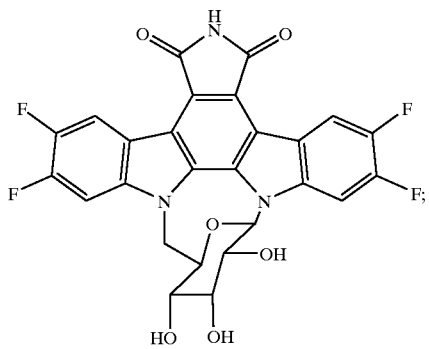
-continued
b.
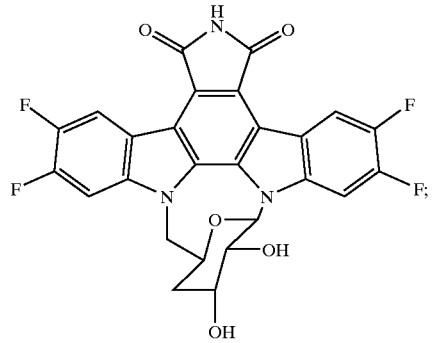
c.
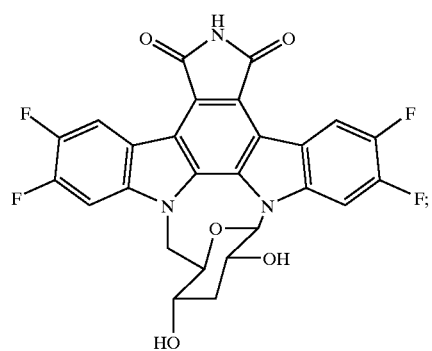
d.
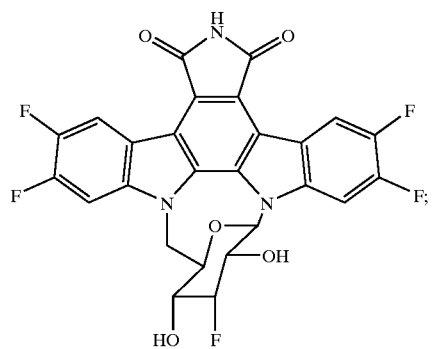
e.
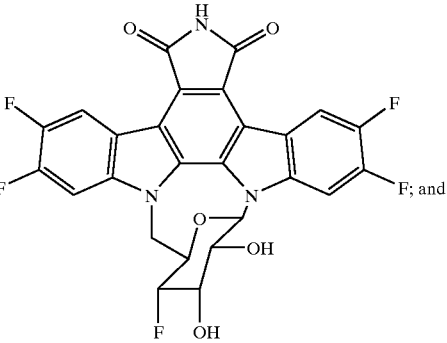
; and f.
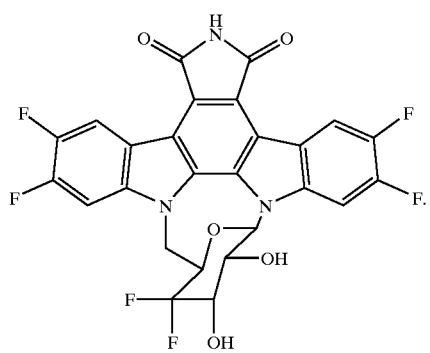
7. A compound selected from the group consisting of:
a.
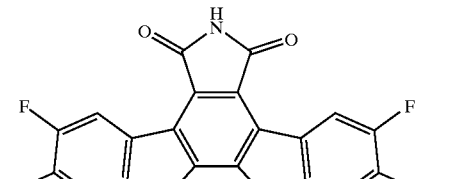
b.
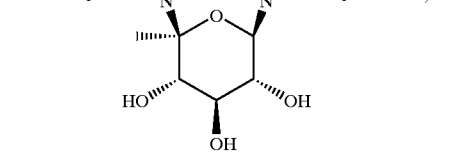
8. A compound selected from the group consisting of:
a.
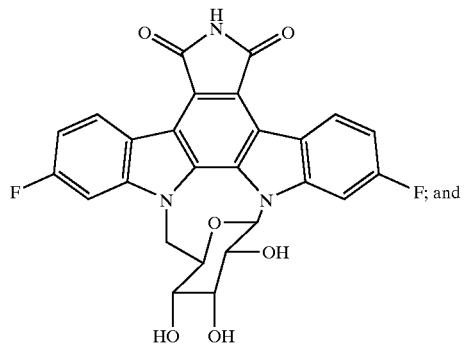
b.
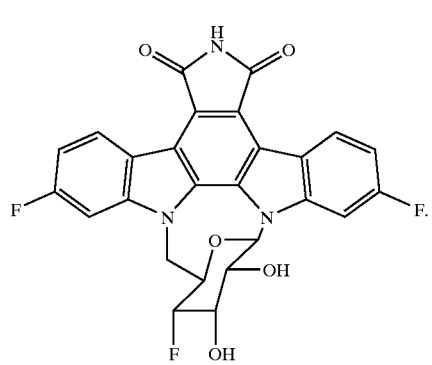
9. A compound selected from the group consisting of:
a.
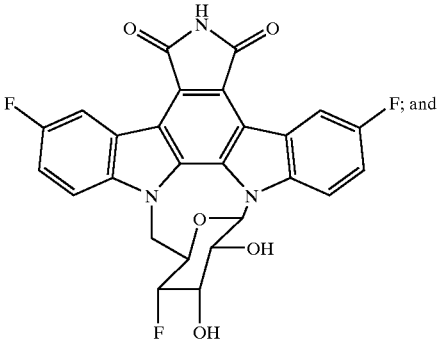
b.
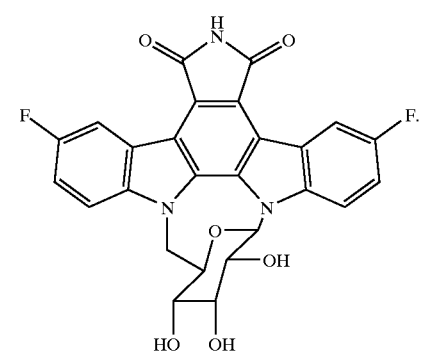
* * * * *